(12) United States Patent
Casorati et al.

(10) Patent No.: US 6,399,054 B1
(45) Date of Patent: Jun. 4, 2002

(54) METHOD FOR THE PRODUCTION OF ACTIVATED MARKED TUMOR-SPECIFIC T CELLS AND USE THEREOF IN TREATMENT OF TUMORS

(75) Inventors: Giulia Casorati; Paolo Dellabona, both of Milan (IT)

(73) Assignee: Science Park RAF S.p.A., Milan (IT)

( * ) Notice: Subject to any disclaimer, the term of this patent is extended or adjusted under 35 U.S.C. 154(b) by 0 days.

(21) Appl. No.: 09/161,998

(22) Filed: Sep. 29, 1998

Related U.S. Application Data

(63) Continuation-in-part of application No. PCT/EP97/01541, filed on Mar. 26, 1997.

(30) Foreign Application Priority Data

Mar. 30, 1996 (EP) .............................. 96105157

(51) Int. Cl.[7] ........................ A61K 35/00; C12N 15/85; C12N 15/63; C07K 16/00; C07K 14/00
(52) U.S. Cl. ................... 424/93.21; 435/320.1; 435/325; 530/387.3; 530/387.9; 530/388.8; 530/388.85; 530/391.1; 530/350
(58) Field of Search .................... 424/93.21; 530/387.3, 530/387.9, 388.8, 388.85, 391.1, 350; 435/320.1, 325

(56) References Cited

FOREIGN PATENT DOCUMENTS

EP          0 496 074         12/1990

OTHER PUBLICATIONS

Restifo et al. (1993) J. Immunother., vol. 14, 182–190, 1993.*
Cavallo et al. (1995) Eur. J. Immunol., vol. 25 (5), 1154–1162, 1995.*
International Publication No. WO 95/03408 published Feb. 2, 1995.
International Publication No. WO 87/04628 published Aug. 13, 1987.
The Journal of Immunology, vol. 149, No. 4, Aug. 15, 1992, pp. 1115–1123, "Involvement of CD28 in MHC–Unrestricted Cytotoxicity Mediated by A Human Natural Killer Leukemia Cell Line".

* cited by examiner

Primary Examiner—Deborah Crouch
Assistant Examiner—Anne Marie S. Beckerleg
(74) Attorney, Agent, or Firm—Arent Fox Kintner Plotkin & Kahn, PLLC

(57) ABSTRACT

A method for the production of activated tumor-specific T cells by co-cultivating, ex vivo, tumor cells from a patient with T cells from that patient, comprising the steps of: i) incubating the tumor cells with a first fusion protein obtained from a B7 protein and one partner of a biological binding pair and a second fusion protein obtained from an antibody against a cell surface antigen and the other partner of the biological binding pair, ii) inhibiting the proliferation of the tumor cells prior to or after that incubation; iii) co-cultivating the tumor cells with the T cells to be activated, until activation of the T cells is attained; iv) separating the activated T cells from the tumor cells, is highly efficient and can be carried out in a simple manner.

50 Claims, 12 Drawing Sheets

Fig. 2
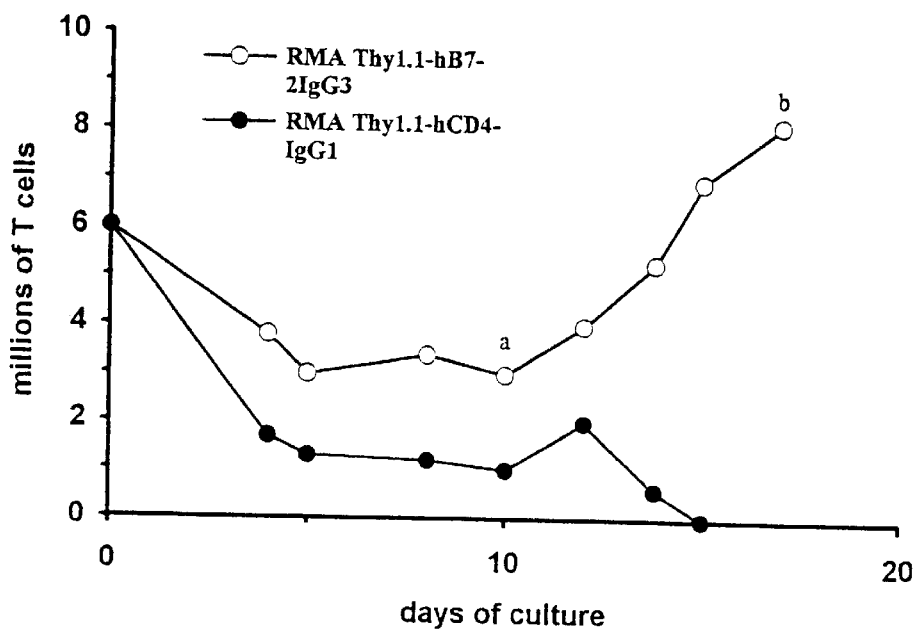
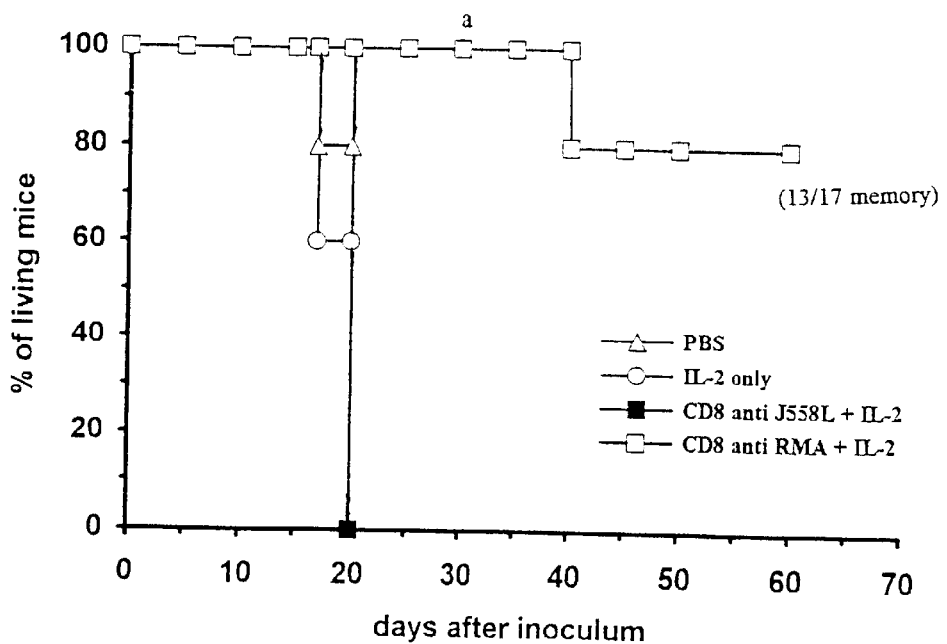

Fig. 3
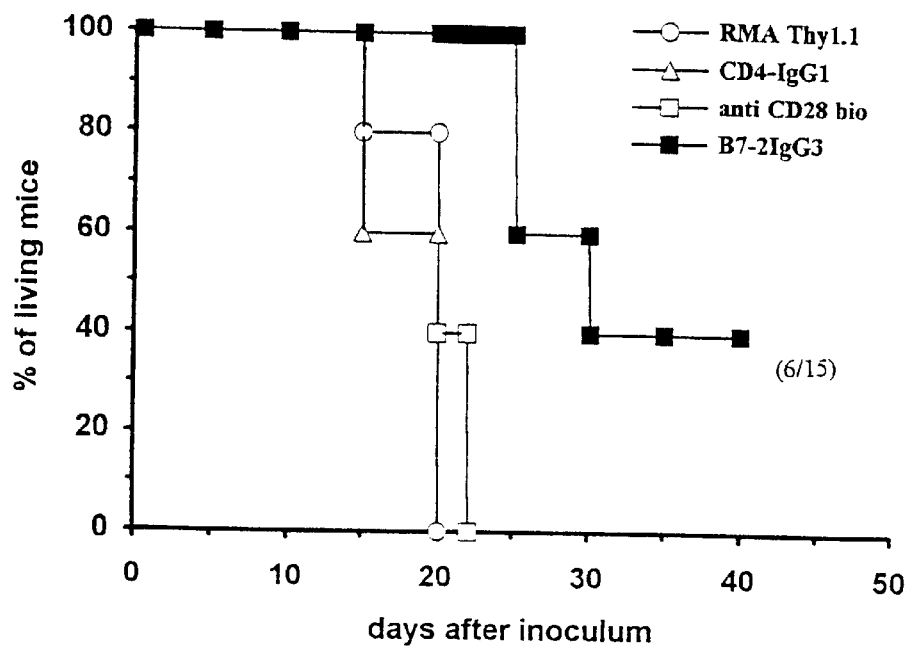
A
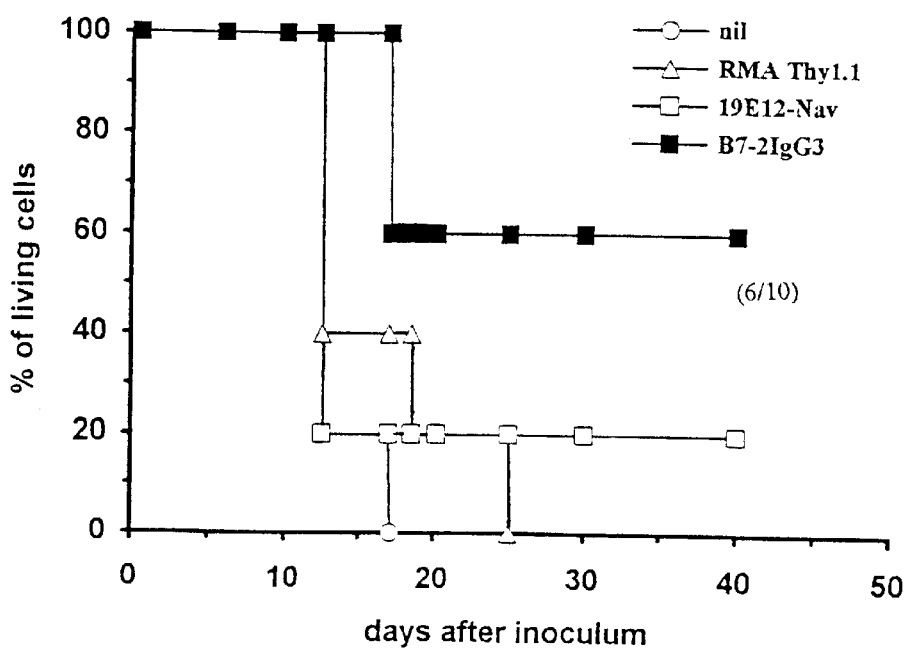
B

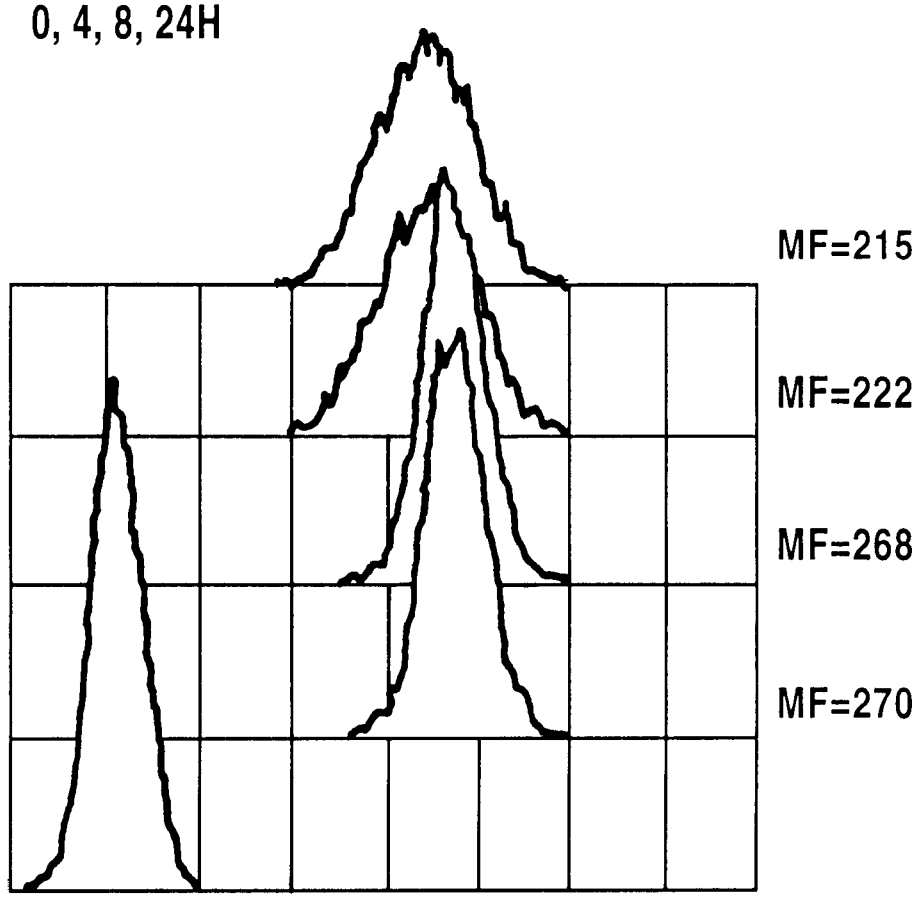

SEQUENCE LISTING

<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: 5' Primer Oligonucleot ide used to clone the extra-cellular region of hB7-2

<400> SEQUENCE: 1
gatatgagct cacagcagaa gcag                                        24

<210> SEQ ID NO 2
<211> LENGTH: 23
<212> TYPE: DNA
<213> ORGANISM: Artificial Sequence
<220> FEATURE:
<223> OTHER INFORMATION: 3' Primer Oligonucleot ide used to clone the extra-cellular region of hB7-2

<400> SEQUENCE: 2
acttacctga gctctggggg agg                                         23

METHOD FOR THE PRODUCTION OF ACTIVATED MARKED TUMOR-SPECIFIC T CELLS AND USE THEREOF IN TREATMENT OF TUMORS

CROSS REFERENCE TO RELATED APPLICATION

This application is a continuation-in-part of International Application PCT/EP97/01541, filed Mar. 26, 1997, and designating the U.S.

The invention is concerned with a method for the production of activated marked tumor-specific T cells by co-cultivating tumor cells from a patient with T cells from that patient, a therapeutic composition containing such activated T cells as well as the use thereof in tumor therapy.

Tumor-specific T lymphocytes recognize peptides derived from proteins synthesized by tumor cells and presented on their cell surface by MHC molecules (Lurquin et al., Cell 58 (1989) 293 and Hellström, K. E., et al., The Biologic Therapy of Cancer, J. B. Lippincot Co., Philadelphia (1991) p. 35). However, T cells require two activating signals to express full effector functions (Mueller, D. L., et al., Annu. Rev. Immunol. 7 (1989) 445). Signal 1 is generated when the T cell receptor (TCR) interacts with the MHC peptide complex. Signal 2 is provided by costimulatory molecules expressed by professional antigen-presenting cells (APC). Many tumors, particularly those of non-hematopoietic origin, do not express costimulatory molecules and thus fail to activate tumor-specific T lymphocytes (Chen, L., et al., Immunol. Today 14 (1993) 483). This finding has provided a rationale for the introduction of genes encoding costimulatory molecules into tumor cells to increase their immunogenicity and vaccination potential.

Among the different costimulatory molecules, B7 proteins (e.g. B7-1, B7-2 and B7-3) are of particular interest since they are expressed on professional APC (Vandenberghe, P., et al., Int. Immunol. 3 (1993) 229; Guinan, E. C., et al., Blood 84 (1994) 3261–3282; WO 95/03408). These costimulatory molecules interact with CD28 and CTLA4 counter-receptors expressed on most T cells leading to a marked increase of IL-2 production, proliferation and acquisition of effector function in both $CD4^+$ and $CD8^+$ T cells (Azuma, M., et al., J. Immunol. 115 (1993) 2091). Blocking the ligation of B7 with a soluble CTLA4-Ig chimeric molecule provokes unresponsiveness in vitro, which has dramatic suppressive effects on the humoral response and graft rejection in vivo. In addition, it has been shown that the transfection of the B7-1 gene into different mouse tumor lines can lead, in some cases, to both their primary rejection and the establishment of a protective immunity (Chen, L., et al., J. Exp. Med. 179 (1994) 523 and Ramarathinam, L., et al., J. Exp. Med. 179 (1994) 1205). However, these studies have revealed a limited efficiency of B7-1 activity on T cell-dependent tumor immunity.

The efficiency of B7 costimulation of anti-tumor T cells is enhanced by cooperation between B7 and ICAM-1, whereby an efficient tumor-specific immune response is stimulated. This effect is dependent on the recruitment of a potent inflammatory reaction (Cavallo, F., et al., Eur. J. Immunol. 25 (1995) 1154–1162).

Molecules of the B7 family are CD28 counter-receptors expressed on APCs. B7-1 was characterized and sequenced in Freeman, G. J., et al., J. Immunol. 143 (1989) 2714–2722. B7-2 and B7-3 were characterized and sequenced in Freeman, G. J., Science 262 (1993) 909–911 and WO 95/03408. The B7 molecules are members of the Ig supergene family with two Ig-like domains (IgV and IgC) and a transmembrane domain. It is suggested that the B7 molecules exist as a monomer or a homodimer on the cell surface, but little, if any, evidence suggests that it can form a heterodimer with CD28 (Lindsten, T., et al., J. Immunol. 151 (1993) 3489). The B7 molecules have a higher affinity for CTLA-4 than for CD28. The genes of the B7-1 and B7-2 molecules have been localized to chromosomal region 3q13.3–3q21. Though these molecules were not highly homologous at the DNA level, they share the identical Ig supergene family structure and the ability to bind to CD28 and CTLA-4, as mentioned above.

However, it was found that B7-1 and B7-2 differ in their appearance after B cell activation. B7-2 appears on the cell surface within 24 hours of B cell activation and B7-1 appears later (Boussiotis, V. A., et al., Proc. Natl. Acad. Sci. USA 19 (1993) 11059). It was further found that in unstimulated human monocytes B7-2 is constitutively expressed whereas B7-1 expression is induced after activation (Azuma, M., et al., Nature 366 (1993) 76). B7-3 is also described in Boussiotis et al. B7-3 has not yet been molecularly cloned.

In WO 95/03408 it is suggested to modify a tumor cell to express B7-2 and/or B7-3 by a transfection of the tumor cell with the nucleic acid encoding B7 in a form suitable for expression of B7 on the tumor cell surface. Alternatively, the tumor cell is modified by contact with an agent which induces or increases the expression of B7 on the tumor cell surface. It is further suggested to couple B7-2 and/or B7-3 to the surface of the tumor cell to produce a modified tumor cell. The term "coupling" as used in WO 95/03408 refers to a chemical, enzymatic or other means (e.g. antibody) by which B7-2 and/or B7-3 is linked to a tumor cell such that the costimulatory molecule (B7) is present on the surface of the tumor cell and is capable of triggering a costimulatory signal in T cells. It is further suggested to cross-link B7 chemically to the tumor surface, using commercially available cross-linking reagents. Another approach would be to couple B7-2 and/or B7-3 to a tumor cell by a B7-specific antibody which binds to both the costimulatory molecule B7 and a cell surface molecule on the tumor cell.

The production of activated tumor-specific T cells may be accomplished by co-cultivating tumor cells from a patient, which tumor cells carry, on their surface, such a costimulatory molecule, with T cells from that patient. Modifying such tumor cells with B7 according to the known method involves a number of drawbacks, however, and is rather unsuitable for routine therapy. Transfecting the tumor cells with the nucleic acid encoding a costimulatory molecule usually is not very effective. In addition to this, it is necessary that the transfected and non-transfected cells should be separated, in a laborious procedure, prior to co-cultivation with the activated T cells. McHugh, R. S., et al., Proc. Natl. Acad. Sci. USA 92 (1995) 8059–8063 suggest to introduce B7-1 onto the surface of tumor cells by using a purified GPI (glycosyl-phosphatidyl-innositol) anchored B7-1 molecule (GPI-B-7) which is able to bind its cognate ligand CD28 and incorporate itself into tumor cell membranes after a short incubation. However, the stability of the GPI-B-7 on the surfaces of irradiated tumor cells is limited and the cells do retain only minimal presentation of B7 capable of effective binding to CD28.

Coupling of B7 to a tumor cell by using a B7-specific antibody which binds both the costimulatory molecule and the cell surface molecule of the tumor has also severe disadvantages. B7 antibodies which are described in the state of the art bind to B7 unfortunately in such a way that the binding of B7 to CD28 decreases dramatically or is completely inhibited. The reason for this is that all known anti-B7-1 and anti-B7-2 monoclonal antibodies interact with CD28 and thus inhibit the T cell response (Azuma, M., et al., J. Exp. Med. 175 (1992) 353–360; Azuma, M., et al., J. Immunol. 149 (1992) 1115; Azuma, M., et al., J. Exp. Med. 177 (1993) 845; Caux, C., et al., J. Exp. Med. 180 (1995) 1841–1847).

It is therefore the object of the present invention to provide a method for the production of activated tumor-specific T cells which can be carried out in a simple manner and exhibits a high efficacy.

The subject-matter of the invention is a method for the production of activated tumor-specific T cells by co-cultivating, ex vivo, tumor cells from a patient with T cells from that patient, comprising the steps of i) incubating the tumor cells with a first fusion protein obtained from a B7 protein and one partner of a biological binding pair and a second fusion protein obtained from an antibody against a cell surface antigen and the other partner of the biological binding pair;

ii) inhibiting the proliferation of the tumor cells prior to or after that incubation;

iii) co-cultivating the tumor cells with the T cells to be activated, until activation of the T cells is attained;

iv) separating the activated T cells from the tumor cells.

T cells of a patient are isolated from peripheral blood lymphocytes (PBMC), which have been prepared from buffy coat of normal human blood samples (Dellabona, P., et al., J. Exp. Med. 177 (1993) 1763–1771). After centrifugation, the mononucleic cells are collected and propagated (Dellabona, P., et al., J. Exp. Med. 177 (1993) 1763–1771). From this preparation, $CD4^+$ and/or $CD8^+$ lymphocytes can be isolated by means of magnetic activated cell sorting (MACS).

The T cells which are used for activation can be generated from a patient according to known methods, preferably by a simple passage of PBMC on any long wool column, whereby B cells and monocytes are excluded (Julius, M. H., et al., Eur. J. Immunol. 3 (1973) 645). $CD8^+$ (with or without $CD4^+$) T cells are purified from the peripheral blood of the patient in vitro by a sorting method, preferably by immunomagnetic sorting. In addition, it is preferred to use a mixed population of tumor-infiltrating T cells (TIL) and purified $CD8^+$ T cells which are obtained from a surgical tumor specimen according to Anichini, A., et al., J. Exp. Med. 177 (1993) 989.

The phrase "activated tumor-specific T cells" preferably denotes tumor-specific T cells which are capable of killing in a specific and restricted manner the tumor cells originally used to activate them. The activation is MHC restricted in the sense of Townsend, A., and Bodmer, H., Ann. Rev. Immunol. 7 (1989) 601.

Generation of tumor specific T cells either total PBMC, or purified $CD8^+$ T cells are cultured in 24-well plates at a ratio of 10.1 to 5.1 with non-replicatig tumor cells (irradiated or mit. C treated or both) which are either autologous or semi-allogeneic, in 2 ml of standard RPMI medium containing 5% human serum, at 37° C. Multiple cultures containing 2 to 5 millions of PBMCs or 1 to 2 millions of $CD8^+$ T cells can be set. The tumor cells have been prepulsed with a saturating concentration (to be determined depending on the different kind of constructs) of soluble B7-1 or B7-2 Ig×antitumor mAb. Recombinant human IL-2 is added to the culture at 5 U/ml at day +5 of the culture and maintained until day +10, after which its concentration is raised to 10 U/ml. At day +15 of the culture, living T cells are recovered from the cultures by a centrifugation over a Ficoll gradient and re-stimulated using the same non-replicating tumor cells prepulsed with the recombinant B7-1 or B7-2 Ig×anti-tumor mAb at a ratio T cell/tumor of 2:1, and a concentration of one million T cells per ml. This restimulation step is performed in 24-well plates, in standard RPMI medium containing human serum supplemented with 2 U/ml recombinant human IL-2. At day +5, the concentration of rhIL-2 is raised to 10 U/ml and maintained as such until day +15.

The T cells can be restimulated a third time as described above, before being tested in a conventional cytotoxicity test (Lanzavecchia, A., Nature 319 (1986) 765–767) against the tumor cells used for re-stimulation in vitro, and unrelated tumor cells for control. The specificity of the T cell line for the tumor is judged according to the level of cytotoxicity shown in the assay. A specific killing activity of about 30–40% can be considered relevant for therapeutic interest. In this case, the tumor specific polyclonal T cell line can be expanded further using a polyclonal activator: PHA in the presence of irradiated allogeneic feeder cells (allogeneic PBMC) and 10 U/ml of rhIL-2; or anti-CD3 mAb+B7-1 IgM and 10 U/ml rhIL-2. At day +15 of restimulation, rhIL-2 is raised to 20 U/ml for 5 days and then to 50 U/ml for another 5 days. By different cycles of restimulation it is possible to reach the desired number of activated T cells to be reinfused in the patient.

In a preferred embodiment, the proliferation of the tumor cells is inhibited prior to or after the incubation according to step i). This may be accomplished, for instance, by means of irradiation or by use of mitomycin C. For irradiation, preferably 3000–5000 Rad are used for inhibition with mitomycin C. preferably 50–100 µg/million of cells are used. Mitomycin C is preferred for inhibition because it prolongs the survival of tumor cells during re-stimulation of T cells.

In a further preferred embodiment of the invention, the activated T cells are marked, preferably after activation. Such a market preferably is a molecule which is presented on the surface of the marked cell. It is therefore particularly preferred to transform the T cells with the nucleic acid which codes for a protein which is presented on the surface of said cell. Such cell surface proteins or antigens are, for example, CD24 (J. Cell. Biochemistry Supplement 17E, page 203, abstract S210), LDL or NGF receptor (WO 95/06723).

After autologous transplantation of said activated T cells which are marked with such a gene product it is possible to trace these cells directly after transplantation in the patient. This gene marking will allow to monitor and compare the efficiency of the therapy with activated tumor-specific T cells.

In a preferred embodiment of the invention, the T cells can further be transformed with a suicide gene. Such a gene causes directly or by mediators the death of the infected cell (cf. WO 92/08796 and PCT/EP94/01573) for in vivo-specific elimination of these cells after successful therapeutic treatment. For this purpose, there is preferably applied the thymidine kinase gene, which confers to the transduced activated T cells in vivo sensitivity to the drug Gancyclovir for in vivo-specific elimination of cells. If, for example, the patient develops signs of an acute incompatibility of the activated T cells, for example like a graft versus host disease (GVHD), with increasing liver function enzymes and a positive skin biopsy, it is preferred to administer i.v. two doses of about 10 mg/kg of the drug Gancyclovir. This results in a reduction of marked activated T cells without a considerable reduction of other lymphocytes.

The diphtheria toxin gene is also preferred as a suicide gene, which is described in WO 92/05262. For the in vivo-specific elimination of the activated T cells, it is also possible to induce a cell apoptosis. It is thus preferred to use a modified FAS receptor and a dose of a related ligand.

The tumor cells of the patient are taken from a surgical specimen. An aliquot of tumor cells can be used to regenerate a tumor cell line either in vitro or in vivo in immunodeficient mice, for subsequent stimulation of T cells. The rest of the fresh tumor cells are used for the direct stimulation of the T cells. Such tumor cells are, for example, melanoma, carcinoma (e.g. breast, cervix, head and neck, colon, lung, kidney, stomach), sarcoma, lymphoma or leukemia.

The term "biological binding pair" is understood to mean a combination of two molecules which have a high specific binding capacity with respect to one another. Such binding pairs are, for example, biotin/avidin (or streptavidin/neutravidin), or sugar/concanavalin A. Preferably, the affinity constant of the binding is kd<1 nmol/l. Preferably, higher affinity constants are applied. For this reason, the biotin/avidin or streptavidin interaction is preferred because of their high affinity. This interaction is stronger than any other receptor ligand in a body. Therefore, it can be used in vivo to conjugate two components of a bifunctional reagent. Methods of biotinylatin are described in Harlow, E., and Lane, D., Antibodies, Cold Spring Harbor Laboratory (1988) 341. Biotinylation or cross-linking with avidin or streptavidin or neutravidin is carried out according to the methods well-known to one skilled in the art.

A preferred technique for pairing two protein molecules is chemical crosslinking, which forms a stable covalent bridge. Many bifunctional crosslinkers are commercially available. There is particularly preferred SPDP (N-succinimidyl-3-(2-pyridyldithio)propionate) crosslinker.

As B7 protein, part of all of B7, preferably of B7-1, B7-2 or B7-3 can be used. Preferably, there are used parts of B7 proteins which include at least the N-terminal variable domain. There are particularly preferred B7-1 or B7-2 proteins and derivatives as described in WO 95/03408, which is for this matter incorporated herein by reference. Since the binding of the B7 fusion protein to the cell surface is effected via the interaction between the biological binding pair and the binding of the anti-surface antigen-antibody, it is not necessary that the B7 molecule should still contain the transmembrane domain.

The second fusion protein contains an antibody against a cell surface antigen and the other partner of the biological binding pair. As antibodies, antibodies that are directed against a great number of cell surface antigens can be used. Those cell surface antigens need not necessarily be tumor cell-specific surface antigens. For this reason, it is preferred to use antibodies against surface antigens which occur to a large extent on cell surfaces, such as ERB B2 or the transferring receptor. It is also possible, however, to use antibodies against suitable tumor-associated antigens like CEA for colon carcinomas, lung carcinomas, mammary carcinomas, CD33 for myeloid leukemias; CD19/CD20 CALLA and CD38 for B cell leukemias, lymphomas, myelomas; Met for gastric carcinomas; OVCA (MOV-18) for ovarian carcinomas; or melanoma-specific antigens.

Preferably, co-cultivation of the activated tumor cells with the T cells is carried out in the presence of small doses of lymphokines (such as IL-2, IL-6, IL-7) which, in addition, are capable of stimulating T cells well. Several rounds of re-stimulation are preferred in order to expand to large numbers tumor-specific effector T cells. Three to four days after the last re-stimulation in vitro, the tumor effector T cells are reinoculated i.v. into the patient. The number of T cells that must be transferred into the patient is variable and can be found out according to established protocols. Preferably, one i.v. infusion for four weeks, consisting of $10^7$–$10^9$ cells/sq.m of body surface area, is used. Established protocols are described, for example, in Greenberg, P. D., Adv. Immunol. 49 (1991) 281–355, and Riddel, R. R., et al., Science 257 (1992) 238–241. At the time of adoptive transfer, patients can be vaccinated with immunogenic tumor cells as well as treated with soluble recombinant tumor-specific B cell molecules to provide further re-stimulation in vivo. This can be achieved by injecting i.v. in the patients a predetermined amount of the soluble B7 conjugate, whereby the mAb binds to the surface of the cells of the tumor diagnosed. If the tumor expresses more than one suitable marker, more than one B7×anti-tumor mAb molecule can be injected into the patient. The amount of soluble reagents and the schedule of injections are determined during the preclinical and clinical trails using, for instance, radio-labeled proteins to monitor its clearance and the efficiency of targeting into the tumor mass. All the essential parameters for this kind of treatment must be derived from the conventional experience of pharmacological and nuclear medicine and are not difficult to find out. It will also be essential to monitor the neutralizing antibody response that the patients can mount against the recombinant proteins.

As mentioned above, it is preferred to monitor the activated T cells in vivo after application. In this case, the adoptive immunotherapy is based on ex vivo expansion of tumor-specific T cells, which are marked preferably with LNGFR and reinnoculum into a patient, preferably together with the tumor-specific soluble B7 conjugate. In this case, the soluble B7 conjugate will re-stimulate transferred tumor-specific effector T cells at the site of the residual tumor mass, allowing the optimal amplification in vivo of the immune response. In fact, in the absence of soluble B7 conjugates (or in the absence of another adequate costimulation), the transferred antitumor T cell blast may perform fewer cycles of killing, after which they can be functionally inactivated or physically eliminated by programmed cell death. The marking of the tumor-specific T cells transferred during the adoptive immunotherapy may allow to monitor the efficiency of this approach by determining the persistence in the patient of transferred T cells.

Also within the scope of the scope of the invention is a kit for treating a tumor in a patient, wherein the kit comprises a fused protein. The fused protein comprises a first fusion protein and a second fusion protein linked by the two partners of the biological binding pair defined above bound together. The first fusion protein comprises an antibody against a cell surface antigen of the patient or at least two Fab fragments of the antibody and one partner of a biological pair. The second fusion protein comprises the other partner of the biological binding pair and a B7 protein. The fused protein can be prepared by incubating the first and second fusion proteins together to form the fused protein, followed by isolation of the fused protein using a method known in the art for separating biomolecules based on a difference in size. Examples of the isolation method include ultrafiltration, chromatography and electrophoresis.

In a preferred embodiment, the kit further comprises an inhibitor of tumor cell proliferation and/or at least one lymphokine. Preferred lymphokines are IL-2, IL-6 and IL-7. The "inhibitor of tumor cell proliferation" is a substance which is capable of inhibiting the proliferation of tumor cells. Examples of the inhibitor of tumor cell proliferation are anti-tumor drugs, such as alkylating agents (e.g. mechlorethamine), antimetabolites, folic acid analogs (e.g. methotrexate), pyrimidne analogs (e.g. 5-fluorouracil), vinca alkaloids (e.g. vinblastine), epipodophyllotixins, dactinomycin, daunorubicin, doxorubicin, bleomycin, plicamycin, mitomycin C, L-asparaginase, interferon, cisplatin, carboplatin, mitoxanthrone, hydroxyurea, procarbazine, mitotane, aminoglutethimide, prednisone, hydroxyprogesterone, diethystibestrol, tamoxifen, testosterone proprionate, flutamide, and leuprolide.

Also within the scope of the invention is a kit for treating a tumor in a patient, wherein the kit comprises a fused protein. The fused protein comprises a first fusion protein and a second fusion protein linked via a linking group. The linking group comprises a partner B of a biological binding pair as defined above, with the two partners of the biological binding pair referred to as partner A and partner B in this embodiment. In other words, the fused protein comprises a first fusion protein, partner B, and a second fusion protein. The first fusion protein comprises an antibody against a cell surface antigen of the cells of the tumor to be treated or at least two Fab fragments of said antibody and partner A. The second fusion protein comprises partner A and a B7 protein. Examples of partner A and partner B are (I) biotin ad avidin, streptavidin or neutravidin or (II) sugar and concanavalin A. Preferably, partner A is biotin and partner B is avidin, streptavidin or neutravidin. The B7 protein can be B7-1 or B7-2. The fused protein can be prepared by incubating the first fusion protein, partner B and the second fusion protein together, followed by isolation of the fused protein based on the size of the fused protein using a known method, such as ultrafiltration, chromatography or electrophoresis. In a preferred embodiment, the kit further comprises an inhibitor of tumor cell proliferation and/or at least one lymphokine. Preferred lymphokines are IL-2, IL-6 and IL-7. The "inhibitor of tumor cell proliferation" is a substance which is capable of inhibiting the proliferation of tumor cells. Examples of the inhibitor of tumor cell proliferation are anti-tumor drugs disclosed above.

Also within the scope of the invention is a method of using one of the above kits in treating a tumor of a patient by administering an effective amount of the fused protein in the kit to the patient. The above kits can be used in a method to treat a tumor in a patient by targeting tumor cells from the patient. The method comprises obtaining T cells and cells from the tumor to be treated from the patient. The proliferation of the tumor cells is inhibited and the tumor cells are incubated with the fused protein of the kit to obtain targeted tumor cells. Preferably, the proliferation of the tumor cells is inhibited before or after the incubation with the fused protein. The T cells are then co-cultivated with the targeted tumor cells to activate the T cells. The activated T cells are separated from the targeted tumor cells to obtain activated tumor-specific T cells, which are administered to the patient to stimulate immunity of the patient against the tumor in order to treat the tumor. Preferably, the activated tumor-specific T cells are administered via intravenous infusion. The amount of activated tumor-specific T cells to be administered would depend on the type of tumor to be treated and the physical condition of the patient. One skilled in the art would know how to adjust the amount to be administered. The preferred amount of activated tumor-specific T cells to be administered is about $10^7$ to about $10^9$ activated tumor-specific T cells per square metet of body surface area of the patient.

Another aspect of the invention are activated tumor-specific T cells. Said activated tumor-specific T cells are activated by tumor cells targeted with a B7 protein. The targeted tumor cells have a B7 protein stably attached to the surface of the tumor cells. The activated tumor-specific T cells are prepared by one of the above disclosed methods. The activated tumor-specific T cells can be used by treating the tumor after administration of an effective amount of the T cells to the patient. The prefered amount of activated tumor-specific T cells to be administered is about $10^7$ to about $10^9$ activated tumor-specific T cells per square metet or body surface area of the patient.

The following examples and the drawing are provided to aid the understanding of the present invention, the true scope of which is set forth in the appended claims. It is understood that modifications can be made in the procedures set forth without departing from the spirit of the invention.

FIG. 1 describes the proliferation of human primary CD4$^+$CD45R0$^+$ T cells costimulated by recombinant soluble B7-Ig molecules (A: anti-CD3; B: anti-CD3$^+$b7-21gG3; C: anti-CD3$^+$B7-11gG1).

FIG. 2A describes the survival of tumor-specific T cell lines. Anti-tumor autologous CTL line can be induced, maintained an expanded in vitro only by B7-2 IgG3 targeted RMA -Thy1.1 cells, and not by control targeted CD4-IgG1 cells. (a: re-stimulation; b: adoptive transfer)

FIG. 2B describes that a specific ant-RMA T cell line but not an anti-J558L T cell line efficiently cures mice inoculated with RMA lymphoma cells. The CTL lines, induced and propagated in vitro by RMA-Thy1.1 cells targeted with B7-2-IgG3 molecules, have 100% therapeutic activity when adoptively transferred into mice bearing an established RMA tumor. Furthermore, 80% of the cured mice develop a systemic immunity against a subsequent challenge with RMA cells. (a: challenge with wt RMA; mice are treated with: PBS/IL-2 only/CD8 anti-J558L+IL-2/CD8 anti-RMA +IL-2).

FIG. 3A describes the survival of mice inoculated with B7-2 IgG3 pre-targeted RMA Thy1.1 living cells. Primary rejection of 40% of mice challenged with lining RMA-Thy1.1 cells, pre-targeted in vitro by three-step produces with B7-2-IgG3.

FIG. 3B describes the therapeutic efficacy of B7-2 IgG3 targeted, non-replicating RMA Thy1.1 cells. Only non-replicating RMA Thy1.1 cells, pre-pulsed in vitro by three-step with B7-2-IgG3 can cure 60% of mice bearing an established tumor.

FIG. 4A describes the three-step method based on the sequential administration of (1) biotinilated anti-Thy1.1 mAb 19212 F(ab)2 fragment (mAb bio 19E12); (2) avidin (NAV); and (3) biotinilated hB7-2-IgG3 (bio-B7-2-Ig).

EXAMPLE 1

Figure 1:
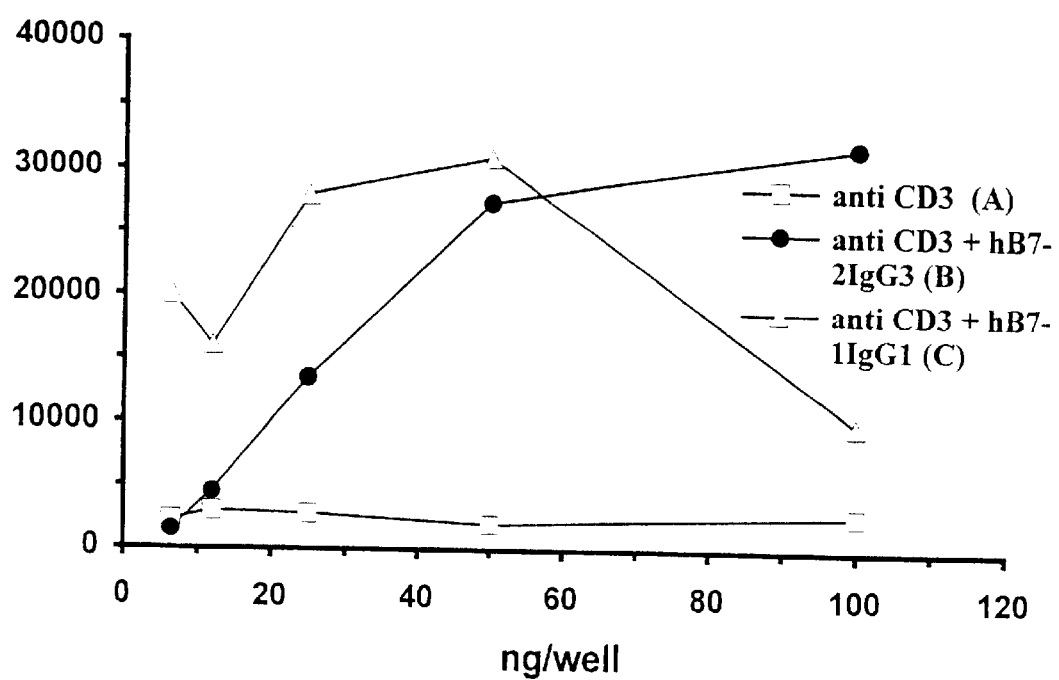

Soluble B7-1IgG1 and B7-2IgG2 Costimulate Proliferation of Primary $CD4^+CD45R0^+$ Human T Cells Purified soluble recombinant B7-1Ig and B7-2Ig molecules (Traunecker, A., et al., Immunology Today 10 (1989) 29–31 and Traunecker, A., et al., Nature 331 (1988) 84–86) were tested for their ability to costimulate proliferation of highly pure human primary $CD4^+CD45R^+$ T lymphocytes. T cells were activated with suboptimal concentration of anti-CD3-specific antibody in the presence of increasing concentration of soluble B7-1Ig or B7-2Ig cross-linked to plastic well. As shown in FIG. 1, both the soluble B7 molecules costimulate in a dose response manner the proliferation of human primary T cells.

EXAMPLE 2

Soluble B7-1IgG1 Costimulates the Acquisition of Cytolytic Activity in Human Primary $CD8^+$T Cells Against Allogeneic Tumor Target Cells Primary human $CD8^+$ T cells were purified to homogeneity (purity of 90%) by negative depletion of $CD4^+$ T cells, using anti-CD4 mAb and magnetic beads. One million purified $CD^+$ T cells were restimulated in vitro with 5 millions of irradiated Jurkat lymphoma cells, in the presence of insoluble B7-1IgG1 molecules, B7-1IgG1 and IL-2 alone or the control chimeric molecule CD4-IgG1. After 5 days, responding T cells were purified on a Ficoll gradient and tested for cytotoxicity against Jurkat cells at various effector to target ratios. FIG. 2 shows that CD8+T cells stimulated by Jurkat cells in the presence of both B7-1IgG1 and IL-2 kill the target more efficiently than IL-2 alone. Thus, soluble B7-1Ig molecules are able to induce the acquisition of effector function in CD8+T cells.

EXAMPLE 3

Biotinylation of Antibodies

Biotinylations are performed using a succinimide ester of biotin. The coupling is done through free amino groups on the antibody or other protein, normally lysyl residues. A solution of N-hydroxysuccinimide biotin at 10 mg/ml in dimethyl sulfoxide and an antibody solution of at least 1–3 mg/ml sodium borate buffer (0.1M, pH 8.8) are prepared. If antibodies have been stored in sodium azide, the azide must be removed prior to coupling by dialyzing extensively against the borate buffer to remove. The biotin ester is added to the antibody at a ratio of 25–250 μg of ester per milligram of antibody, mixed well and incubated at room temperature for 4 hr.

High concentrations of the biotin ester will lead to multiple biotin groups binding to the antibody and will increase the probability that all of the antibodies will be labeled. Lower ratios will keep biotinylation to a minimum (25 μg of ester/mg of antibody gives an initial molar ratio of approximately 10:1). 20 μg of 1M $NH_4Cl$ per 250 μg of ester is added an the mixture is incubated for 10 min at room temperature. The antibody solution is dialyzed against PBS or other desired buffer to remove uncoupled biotin. The biotin dialyzed more slowly than would be expected for its size, so extensive dialysis is needed.

EXAMPLE 4

Plasmocytoma Cells Secreting B7-1Ig or B7-2Ig Molecules Induce an Efficient Protective Antitumor Immunity in Syngeneic Mice J558L plasmocytoma clones secreting B7-1IgG1, B7-1IgM, B7-2IgG3, CCD4IgG1, Cd4IgM or CTLA4IgG1 were injected in the right flank of singeneic Balb.c mice and their growth was evaluated. None of the mice challenged with plasmocytoma cells secreting B7-1 or B7-2 molecules developed a tumor mass, whereas tumors developed in all the mice challenged with cells secreting control CD4 or CTLA4 molecules. These results are summarized in Table 1.

Furthermore, all the mice that rejected J558L cells secreting B7 Ig molecules showed a protective secondary response to later challenge with parental plasmocytoma cells (Table 1). Thus, soluble chimeric B7-1 and B7-2 molecules maintain in vivo the capacity to prime an efficient antitumor immunity and to vaccinate animals against tumor onto which they are targeted.

TABLE 1

J558L plasmocytoma cells secreting human B7-1Ig or B7-2Ig can be used to vaccinate syngeneic animals against later challenge with non-transfected parental cells.

| Tumor Type | % of tumor-free mice primary response | % of mice showing memory response |
| --- | --- | --- |
| J558L | 0 | 0 |
| J558L-B7-1IgG1 | 100 | 100 |
| J558L-B7-1IgM | 100 | 100 |
| J558L-B7-2IgG2 | 100 | 100 |
| J558L-B7-CD4IgG1 | 0 | 0 |
| J558L-B7-CD4IgM | 0 | 0 |
| CTLAIgG1 | 0 | 0 |

EXAMPLE 5

Induction of Autologous CTLs

The gene coding for Thy1.1 allele was transfected into two mouse tumorigenic cell lines (T lymphoma RMA and mammary adenocarcinoma TS/A) that are syngeneic to mouse strains that express the Thy1.2 allele (C57.B6 and Balb.c respectively). In this way, once the tumor cells are inoculated into the mice, they will form the only tissue of the mouse expressing the specific tumor marker. It is also preferred to use as the tumor marker the alleles Ly2.1 (CD8) and Ly5.1 (CD45) for improvement of behavior on the tumor cell surface (i.e. easy capping, internalization or shedding). There are used mAbs specific for the desired allelic tumor marker, which will represent the tumor targeting arm. They are used as such, or they can be reduced to −46ab' fragment.

Priming with RMA-Thy1.1+(tri-step)

Non-replicating (irradiated or mitomycin C-treated) RMA or TS/A cells expressing Thy1.1 were pulsed at +4° C. with a saturating dose of biotinylated Thy1.1 specific monoclonal antibody (mAb 19E12). The excess mAb were washed away and an excess amount of Neutravidine (Nav, recombinant avidine from Pierce) was added. The Nav is tetravalent and binds to biotinylated 19E12 mAb while still leaving at least one free binding site for another biotinylated molecule. The excess Nav was washed away and either the biotinylated recombinant B7-1IgG1 or the B7-2IgG3 were added, to complete the three-step bridge. As a control, priming with RMA cells transfected with Thy1.1 was used. After 6 days, the surviving T cells were assayed in a killer assay against parental RMA cells.

The tumor cells had potent costimulatory molecules on their surface in the absence of any genetic manipulation.

The tri-step targeted tumor cells were used to re-stimulate in vitro allogeneic cytolytic CD8+ T cells.

In fact, only cells expressing functional B7-1 or B7-2 on their surface can prime or restimulate autologous effector cell in vitro. The results are shown in Table 2 and FIG. 2.

TABLE 2

The killing is specific, and there is no NK killing on NK-targets (YAK or RMA-S cells).

| Priming with | E/T 100:1 | 50:1 | 25:1 | 12.5:1 | 6:1 | 3:1 |
|---|---|---|---|---|---|---|
| RMA-Thy1.1 + tri-step | 30% | 15% | 12% | 8% | 7% | 5% |
| RMA-Thy1.1 | 5% | 5% | 5% | 4% | 3% | 0% |

E/T = Effector/Target Ratio

EXAMPLE 6

Induction of a Protective Response by Tri-Step Pre-Targeted Tumor Cells

Living tumor cells (e.g., RMA-Thy1.1) pre-targeted in vitro with soluble B7-1 or B7-2 (e.g., B7-2-IgG3) using the tri-step procedure were inoculated subcutaneously (s.c.) into syngeneic mice and scored for rejection. Moreover, non-replicating tumor cells prepulsed in vitro with the tri-step were used to vaccinate mice from a second challenge with a lethal dose of parental cells (for results, see FIG. 3A)

EXAMPLE 7

Induction of a Curative Immunity Against Minimal Tumor Residual Disease

Mice are challenged either s.c. or intravenously (i.v.) with various doses of living tumor cells expressing Thy1.1 allele (or other tumor-specific markers). The tumors are allowed to grow for some days, then they are treated non-replicating RMA-Thy1.1 cells, pre-targeted in vivo by three-step with B7-2-IgG3, the non-replicating, therapeutic cell vaccine is given s.c. twice a week for three weeks (for results, see FIG. 3B).

EXAMPLE 8

Induction of a Curative Immunity Against Minimal Tumor Residual Disease, By Direct In Vivo Three-Step Administration of B7-Ig Molecules Mice are challenged either s.c. or intravenously (i.v.) with various doses of living tumor cells expressing Thy1.1 allele (or other tumor-specific markers). The tumors are allowed to grow for some days, then they are treated with the tri-step in vivo. First, they receive the biotinylated anti-Thy1.1 mab; 12 hours later NAv, and 36 hours later the biotinylated soluble recombinant B7-1 B7-2. The tumor growth is then scored. The in vivo tri-step can be repeated over time and it can be associated with the use of recombinant, biotinylated lymphokines which can synergize with B7-1 or B7-2 (IL-4, IL-7, IL-10, IFN-gamma, IL-12) at the site of the tumor mass.

Induction of a curative response against minimal tumor residual diseases can be achieved by combining in vivo tri-step targeting of soluble B7-1 or B7-2 costimulatory molecules with active vaccination with engineered tumor cells and/or passive transfer of tumor-specific T cell lines expanded in vitro with the in vivo re-stimulation.

The engineered tumor cells used as vaccines can be generated either by transfection with genes coding for B7-1 or B7-2 or by the tri-step pre-targeting procedure. On the same line, tumor-specific T cells can be induced and expanded in vitro following the tri-step protocol described above.

EXAMPLE 9

Targeting Tumors by B7-2-Ig Molecules and its Effects on T Cell Immunity

Female BALB/C and C57BL/6, 4 to 8-week-old mice, were used. The Rauscher virus-induced RMA T lymphoma of C57BL.6 origin (H-$2^b$) and the WEHI 164 fibrosarcoma of BALB/C origin (H-$2^d$) were maintained in vitro at 37° C. in a humidified 5% $CO_2$ atmosphere in air, in complete medium (RPMI 1640 with 5% FCS, 100 U/ml penicillin, 100 U/ml streptomycin and $2.5 \times 10^{-5}$M 2-ME). Cells were not cultured for longer than 3 weeks and routinely screened for Mycoplasma contamination.

Thy1.1 cloning and transfection. Cloning of the mouse (m) Thy1.1 cDNA, as well as methods for transfection, selection, and cloning of transfected RMA cells were performed as described in the art (Moro, M: Cancer Res. 1997). Clones of WEHI 164 Thy1.1 were obtained following the same protocols.

Generation of soluble recombinant B72-IgG3 molecules. The cDNA encoding for the extra cellular region of hB7-2 was cloned by reverse transcription-PCR from the human lymphoma line Raji using the following oligonucleotide: 5'-GATATGAGCTCACAGCAGAACGAG-3' (5' primer), SEQ ID NO:1 and 5'-ACTTACCTGAGCTCTGGGGGAGG-3' (3' primer), SEQ ID NO:2. The PCR product, containing the correct B7-2 sequence, was cloned into the mammalian expression vector pCD4-Hγ3, containing the hIgG3 constant region, after the excision of the CD4 fragment. To express the recombinant molecule, mouse J558L plasmocytoma line was transfected with p-hB7-2-IgG3 by protoplast fusion. Transfected cells were selected with 5 μg/ml mycophenolic acid and 100 μg/ml Xantine, and screened for the expression of hB7-2IgG3 soluble molecule by ELISA test using goat anti-human Ig antiserum. Positive clones were re-cloned, and expanded to large scale culture for production. The hB7-2IgG3 soluble molecule was purified by protein G-sepharose (SIGMA) affinity chromatography.

Preparation of bio-19E12 mAb and bio-hB7-2IgG3. Biotinilation of the anti-Thy1.1 mAb 19E12 was performed as previously described. The 19E12 (Fab)$_2$ fragment was obtained by resuspending purified mAb in 0.1M sodium citrate, pH 4,5 at the final concentration of 2 mg/ml. One ml of mAb solution was mixed with 5 μl of pepsin (SIGMA), 1 mg/ml in 0.1M sodium citrate, incubated 2 hours at 37° C. and dialyzed overnight against 2 liters of 1.5M Glycine, 3M sodium chloride at 4° C. The (Fab)$_2$ fragment was separated from the Fc fragment on a protein A-sepharose column and dialyzed against PBS. This digestion protocol usually yields mostly F(ab)2 fragment, with minor contamination by Fab' fragments, as judged by SDS-PAGE analysis of digestion products. The soluble hB7-2IgG3 was biotinilated as follows: 0,5 mg of hB7-2IgG3 1 mg/ml in sodium bicarbonate, pH 8,5, was mixed with 6 μl of a sulfo-NSH-LC-biotin (Pierce Chemical Co. Rockford, Ill.), 1 mg/ml in water, incubated 30 min at 25° C. and dialyzed overnight against 2 liters of PBS at 4° C. The product (bio-hB7-2IgG3) was kept at 4° C.

In vitro targeting of the bio-hB7-2IgG3 onto RMA Thy1.1 cells. RMA Thy 1.1 cells were resuspended at concentration of $1\times10^6$/ml in 50 μl of PBS/2% FCS in round-bottomed microtiter plate well, mixed with 1 μg of bio-19E12 mAb and incubated for 10 min on ice. After washing, cells were incubated with 1 μg of Neutravidin ( a deglycosylated avidin with neutral isoelectric point from Pierce Chemical Co.) in 50 μl 1 f PBS/FCS on ice for 10 min, washed again, and finally resuspended in 50 μl of PBS/FCS containing 3 μg of bio-hB7-2IgG3. After 10 min on ice, cells were washed and used for experiments.

In vitro priming of tumor specific CTLs. Non replicating RMA-T cells were obtained by incubating $2\times10^7$ cells/ml with 60 μg/ml of Mitomycin C (Mit.C, Sigma) in RPMI 1640 during 30 min at 37° C. Spleen cells from C57BL/6 naive mice were purified on a 20 ml nylon wool column. $CD8^+$ T cells (average 80–90% purity) were purified from nylon wool spleen cells (NWSC) by complement mediated lysis of $CD4^+$ T cells using anti-CD4 mAb GK1.5 and rabbit complement (LowTox Cedarline). CTLs were generated by culturing $10-20\times10^6$ NWSC with non-replicating $2-4\times10^6$ RMA Thy1.1 cells, pre-pulsed with bio-B7-2IgG3 as described above, at 37° C. in a 6 well plate containing 5 ml of complete medium. Five days later blasts were isolated on a lympholyte gradient (Cedarlane, Hornby, Ontario) and resuspended in culture containing 10 U/ml of human recombinant IL-2 (Roche, Basel, Switzerland). In inhibition experiments, an anti CD8 mAb (53.6.72) or purified recombinant hCTLA-4 IgG1 were added to the MLTC at the final concentration of 1 μg/ml. To inhibit MHC class I recognition, 10% of culture supernatant containing anti MHC class I $K^b$ (Y3) or $D^b$ (B22.249) mAbs were added to the MLTC. For the induction of long term anti tumor CTL line, T cells are cultured in medium supplemented with 20–40 U/ml of human recombinant IL-2, and restimulate every 7–10 days with non replicating RMA Thy1.1 cells pre-pulsed with bio hB7gG3.

Cytoxicity assays. At day 6, blasts were tested in a standard 4 h $^{51}$Cr released assay. Target cells were labelled with $^{51}$Cr and used at 1000 cells/well at effector to target ratios ranging from 3:1 to 100:1. The percentage specific of $^{51}$Cr release of triplicates was calculated as (average experimental cpm–average spontaneous cpm)/(average maximum cpm–average spontaneous cpm)×100. $^{51}$Cr release by target cells alone (spontaneous release) was always<25% of maximal $^{51}$Cr release (target cells in 1 N HCl).

Cytofluorimetric studies. The presence of bio-hB7-2IgG3 onto tumor cells after the in vitro or the in vivo targeting was assessed by staining cells with FITC conjugated Goat anti Human IgG antiserum (Southern Biothec. Cat. 2040-02). Tri-colour cytofluorimetric analysis of mouse PBMCs and Spleen cells were performed with the following antibodies: FITC-labelled rat anti-mouse CD8a mAb (Pharmingen cat. 01044D), FITC-labelled mouse anti-mouse Vα3 TCR mAb (Pharmingen cat. 01454C), R-Phycoerythrin-labelled rat anti-mouse CD69L mAb (Pharmingen cat. 01265B), an R-Phycoerythrin-labelled rat anti mouse CD44 mAb (Pharmingen cat. 01225A) and a biotin-conjugated mouse anti-mouse Vb5.1, 5.2 TCR mAb (Pharmingen cat. 01352C), followed by Cychrome-conjugated Strepavidin. The analysis was performed on a FACScan cytofluorimeter (Beckton Dickinson, Palo Alto, Calif.), by gating first on lymphocytes using physical parameters, and acquiring at least 15.000 events.

In vivo studies. To evaluate the therapeutic efficacy of B7-2-Ig targeted, non-replicating RMA cells, mice were challenged s.c. in the left flank with $3\times10^4$ living parental RMA cells. After three days, tumor-bearing mice received twice a week s.c. inocula of $1\times10^6$ Mit.C-treated RMA Thy1.1 pre-targeted with hB7-2 IgG3 or with control molecules. For adoptive transfer experiments, mice were challenged s.c. in the left flank with $3\times10^4$ living parental RMA cells. Three days after, tumor-bearing mice received $10^6$ anti RMA CTLs, together with human recombinant IL-2, administered ip at 2000 U/day for the following three days. For in vivo targeting of bio-hB7-2IgG3, mice were challenged s.c. with $3\times10^4$ RMA Thy1.1 living cells. The three-step targeting started with bio-19E12 mAb (Fab)$_2$ fragment, injected ip at 50 μg/mouse either 24 or 72 hours after the inoculum of tumor cells. In the second step, Neutravidin was injected ip at 30 μg/mouse 24 hours after the administration of the first step. Six hours later, 50 μg of either bio-hB7-2IgG3 or bio-hIgG3 were injected ip into each mouse. In the case of WEHI 164 Thy 1.1, $10^7$ living cells were injected sc into mice, and the three-step treatment was started when the tumor diameter reached 5–7 mm of mean diameter. To evidentiate the development of a memory response, mice that remained tumor free after 30 days from the three-step tumor targeting with B7-2-Ig molecules were challenged counterlaterally with $10^5$ RMA or $10^7$ WEHI 164 parental non-transfected cells, and scored for tumor growth. All experiments performed in vivo were repeated at least twice with groups of 5 to 10 mice, obtaining homogeneous results.

Results of the above experiments are presented below.

Figure 4A:
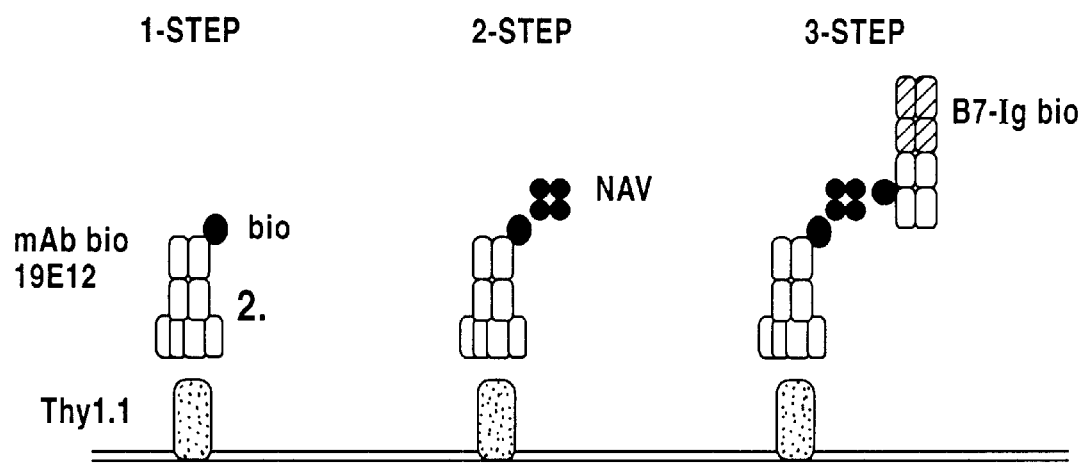
FIG. 4B shows that the three-molecular complex is stably attached to the surface of RMA-T cells.

Stable three-step mediated targeting of B7-2IgG3 onto RMA-Thy1.1 lymphoma in vitro. The RMA lymphoma was chosen as tumor model to study the effects of targeted soluble B7-2-Ig costimulatory molecules, since it is known that it primes CTLs in vitro and is rejected in vivo when transfected with hB7-2 costimulatory molecules. In a preliminary set of experiments, it was established that purified B7-2-Ig molecules were fully functional, both by binding to CHO cells expressing surface CTLA-4 molecules and by costimulating IL-2 production in a mouse T cell hybridoma, activated by a sub-optimal concentration of soluble anti-CD3 mAb. To generate a model tumor associated antigen to use as target structure for the soluble recombinant B7-2-IgG molecules, RMA cells were transfected with a cDNA encoding for the Thy1.1 allele. The RMA lymphoma, in fact, originated in C57BL/6 mice, which express the Thy1.2 allele. Thy1.1 differs from the 1.2 allele by only three aminoacids, and is poorly immunogenic in the mouse strains expressing the 1.2 allele, thus minimizing the danger to increase the intrinsic immunogenicity of RMA cells. Targeting of B7-2-Ig onto RMA-Thy1.1 cells (RMA-T) was achieved by a three step method (FIG. 4-A), based on the sequential administration of : i. biotinilated anti-Thy1.1 mAb 19E12 F(ab)$_2$ fragment (bio-19E12); ii. avidine (NAV); and iii. biotinilated hB7-2-IgG3 (bio-B7-2-Ig). The F(ab)$_2$ fragment of 19E12 mAb was used instead of the whole antibody to prevent the effects originated by its Fc portion. As shown in FIG. 4B, this three molecular complex was stably attached to the surface of RMA-T at 37° C. for at least 24 h.

Figure 5:
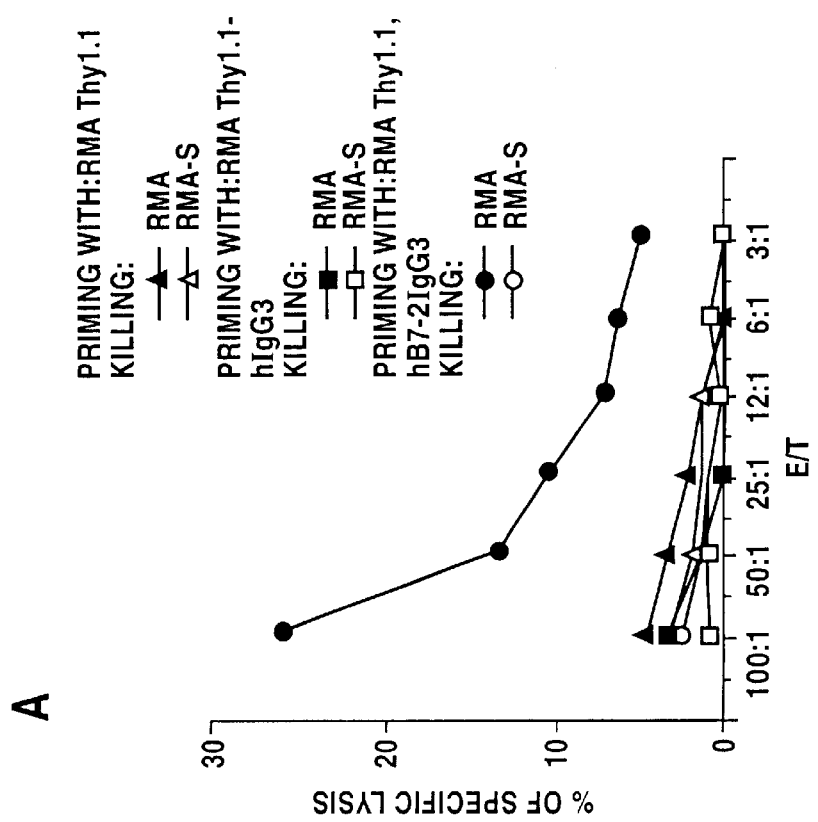
FIG. 5A shows that RMA-T cells pre-targeted bio-B7-2-Ig prime tumor-specific CTLs.
FIG. 5B shows that the priming of naive CTLs was abolished by either soluble CTLA4-Ig or anti-CD8 mAb or anti-D$^b$ mAb during the MLTC.
Figure 6:
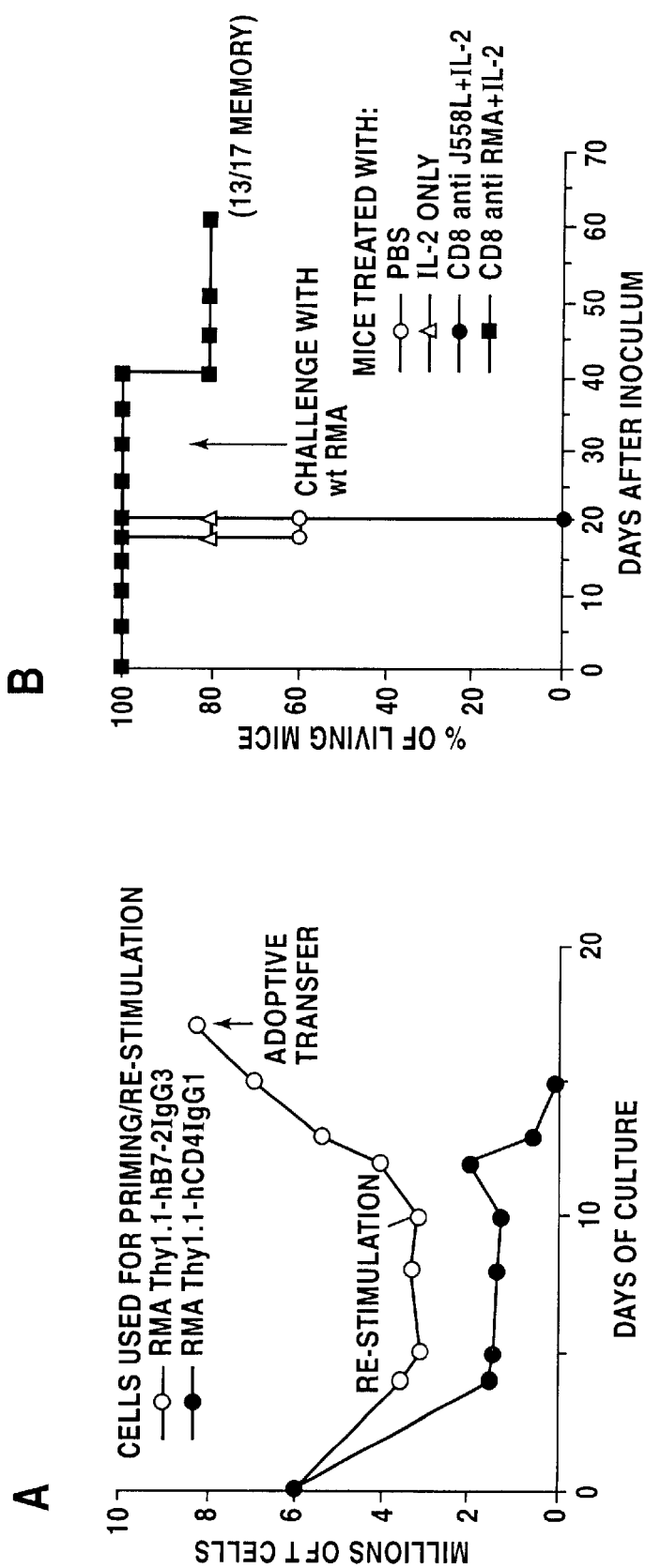
FIG. 6A shows that pre-targeted RMA-T could be used to restimulate the tumor specific CTL lines.
FIG. 6B shows that only T cells primed and restimulated with RMA-T targeted with bio-B7-2-Ig, and not with the allogeneic J558L plasmacytoma line, had therapeutic effect on the established tumors.

RMA-T cells pre-targeted with bio-B7-2-Ig prime specific CTLs which are highly efficient in adoptive immunotherapy. The efficacy of three-step tumor targeting of bio-B7-2-Ig to induce anti-tumor CTL lines suitable for adoptive immunotherapy was first evaluated. RMA-T cells, pre-targeted with bio-B7-2-Ig, were therefore used to prime naive CTLs in vitro. As shown in FIG. 5A, RMA-T cells pre-targeted with bio-B7-2-Ig prime tumor-specific CTLs in vitro. The priming of naive CTLs was abolished by the addition of either soluble CTLA4-Ig, or anti-CD8 mAb or anti-$D^b$ mAb during the MLTC, indicating the requirement for the ectodomain of B7-2, the expression of CD8 on CTLs and that of $D^b$-peptide complexes on RMA, respectively (FIG. 5B). Pre-targeted RMA-T could also be used to efficiently restimulate the tumor specific CTL lines that could be used in adoptive immunotherapy of mice bearing an established RMA tumor (FIG. 6A). At day 15 of the culture, $10^6$ CTLs were transferred into each mouse bearing a 4 day old RMA tumor, generated by the sc injection of $3 \times 10^4$ living cells (3xMTD). As shown in FIG. 6B, only T cells primed and restimulated with RMA-T targeted with bio-B7-2-Ig, and not with the allogeneic J558L plasmacytoma line, had therapeutic effect on the established tumors. Moreover, the majority of mice cured by the adoptively transferred CTL lines rejected a subsequent counterlateral challenge with living RMA cells, indicating the development of a systemic memory response (FIG. 6B).

In vitro pre-targeting of non-replicating RMA-T cells with bio-B7-2-Ig generates efficient therapeutic vaccines.

Figure 7:
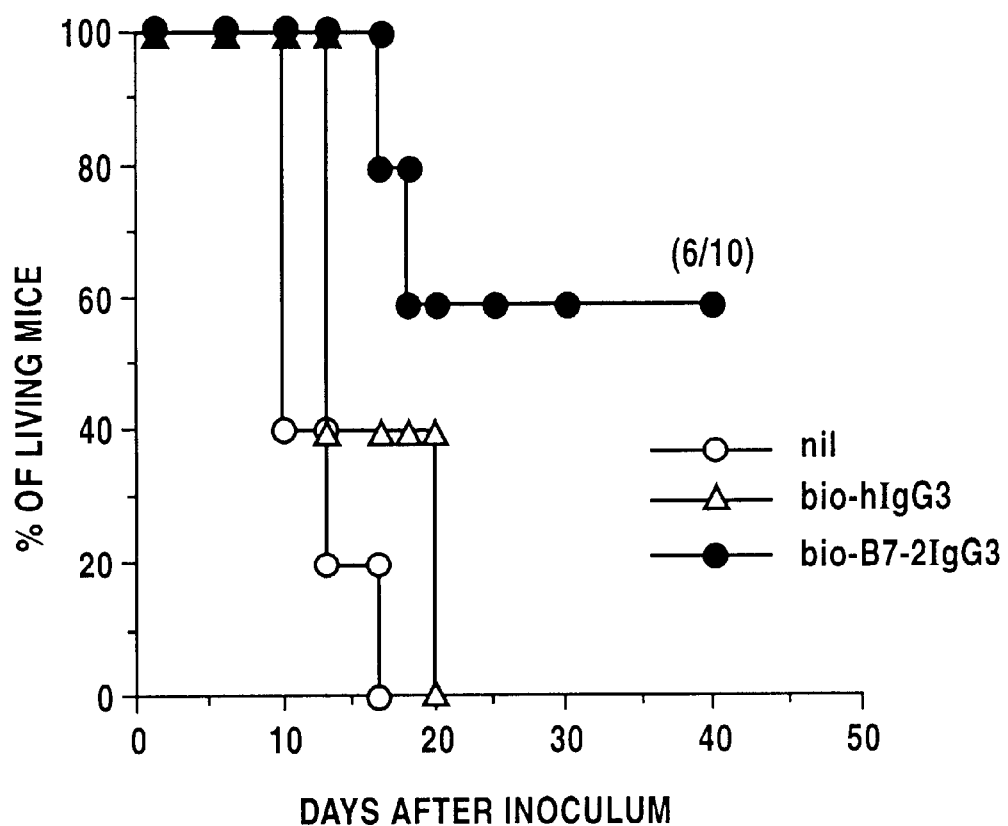
FIG. 7 shows that B7-2-Ig pre-targeted non-replicating RMA-T cells cured a significant number of tumor-bearing mice.

The therapeutic efficacy of tumor vaccines, generated in vitro by pre-targeted non-replicating RMA-T cells with bio-B7-2-Ig, was then evaluated. These vaccines were used to cure syngeneic C57BL/6 mice bearing a 4 day old sc RMA tumor. As shown in FIG. 7, B7-2-Ig pre-targeted non-replicating RMA-T cells cured a significant number of tumor-bearing mice, indicating that tumor pre-targeted in vitro with soluble B7-2-Ig molecules generate highly immunogenic non-replicating cell vaccines for active immunotherapy.

Enhancing anti-tumor response by in vivo targeting of bio-B7-2-Ig onto established tumors.

Figure 8:
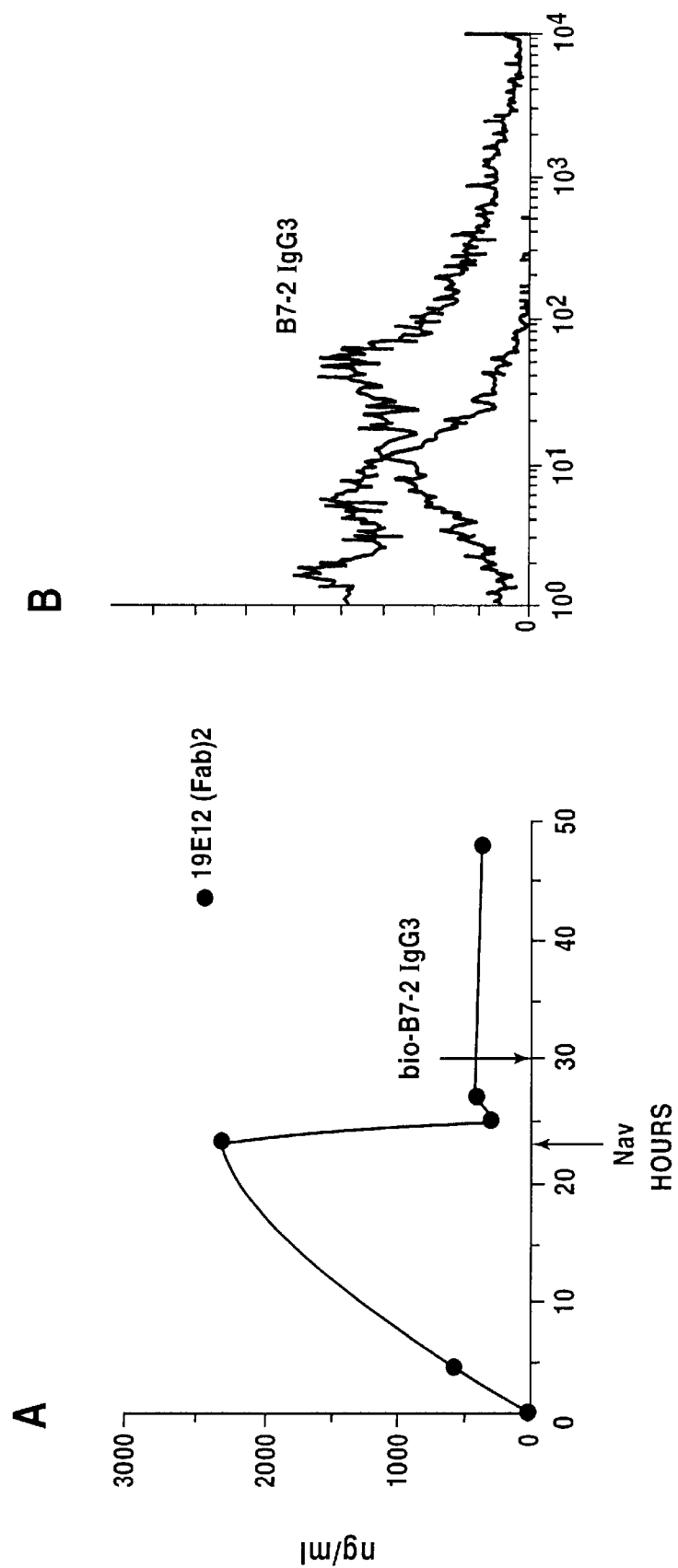
FIG. 8A shows that, after bio-Fab2 19E12 was injected into RMA-T bearing mice and allowed to recirculate for 24 hours, the F(ab)$_2$ fragment reached the highest hematic concentration.
FIG. 8B shows that bio-B7-2-Ig was still present on RMA-T cells 24 hours after its injection into mice.
Figure 9:
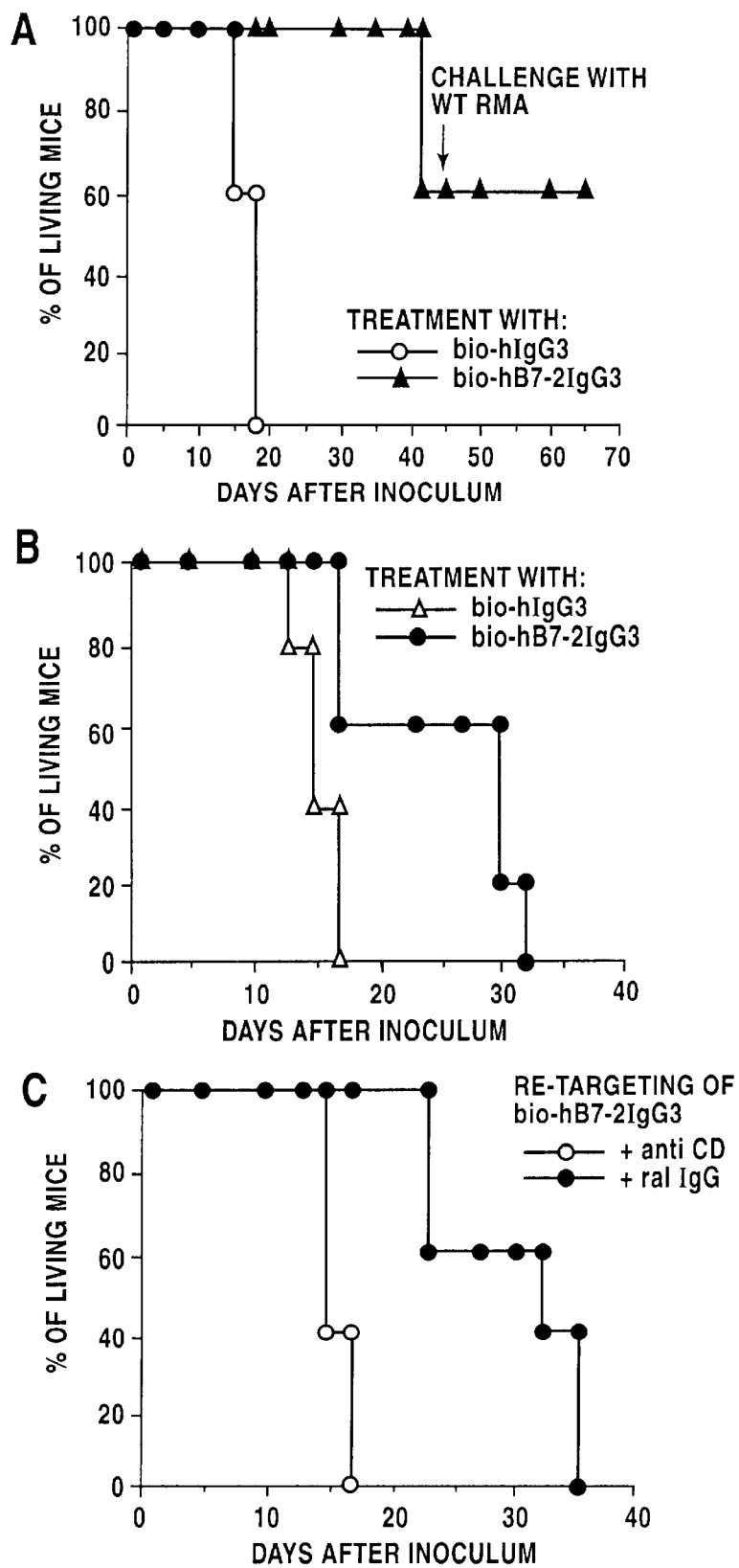
FIG. 9 shows the therapeutic efficacy of a three-step targeting regimen.

The efficacy of in vivo targeting of bio-B7-2-Ig onto established tumors on the induction of a therapeutic immunity was determined. In preliminary experiments, the three-step protocol shown in FIG. 8 was worked out: 50 µg of bio-Fab2 19E12 were injected ip into RMa-T bearing mice at time 0, and allowed to recirculate for 24 hrs. By this time, the F(ab)$_2$ fragment reached the highest hematic concentration, as measured by ELISA (FIG. 8A). In the second step, Av was injected ip into mice 24 hr. later. This caused both the rapid and persistent clearance of bio-19E12 F(ab)2 from circulation (determined by ELISA), and the avidination of the tumor (determined by ex-vivo cytofluorimetric analysis of the tumor, not shown). In the third step, bio-B7-2-IgG3 was finally injected ip 6 hrs after Av injection, corresponding to time +30 hr of the targeting experiment, and its targeting onto RMA-T cells was determined 24 hrs later by cytofluorimetric analysis performed ex-vivo by staining dispersed tumor cells with anti-human Ig antiserum. As shown in FIG. 8B, bio-B-2-Ig was still present on RMA-T cells 24 hr after it was injected into mice. To assess the therapeutic efficacy of this three-step targeting regimen, mice that received a sc inoculum of $3 \times 10_4$ living RMA-T cells were divided into two groups: in the first group, mice received the third step bio-B7-2 at time +52 hrs from tumor inoculum, while in the second group mice received bio-B7-2-Ig at time +102 hrs from tumor inoculum. As shown in FIG. 9A, 60% of the mice of the first therapeutic group rejected the primary tumor. All the mice rejecting the primary tumor following in vivo targeting of B7-2-Ig molecules developed a protective response, and rejected a subsequent counterlateral challenge with living parental RMA cells. In the second therapeutic group, all the mice developed a tumor with significantly slower growing rate (FIG. 9B). The therapeutic efficacy of three-step targeting of bio-B7-2-Ig was confirmed in another tumor system, base on the sc injection of $10^7$ WEHI 164-Thy1.1$^+$ sarcoma cells into BALB/c mice. All the mice which had received bio-B7-2-IgG3 by time +102 hrs were cured, while only 20% of control mice were cured by the administration of bio-Human IgG3 (data not shown).

In vivo tumor targeting by B7-2-IgG3 enhances tumor-specific CD8+ CTLs activity. CD8$^+$ CTLs are the major effectors in the anti-tumor response elicited by tumors transduced with B7 genes. Determination was made as to whether targeting of B7-2-Ig molecules onto established RMA tumors was also elicited a CD8$^+$ tumor specific response. As shown in FIG. 9C, the therapeutic effects of the in vivo targeting of B7-2-Ig were completely abolished by depleting CD8$^+$ T cells from mice before starting the three-step treatment, indicating that involvement of a T cell mediated immunity by the three-step treatment.

Figure 10:
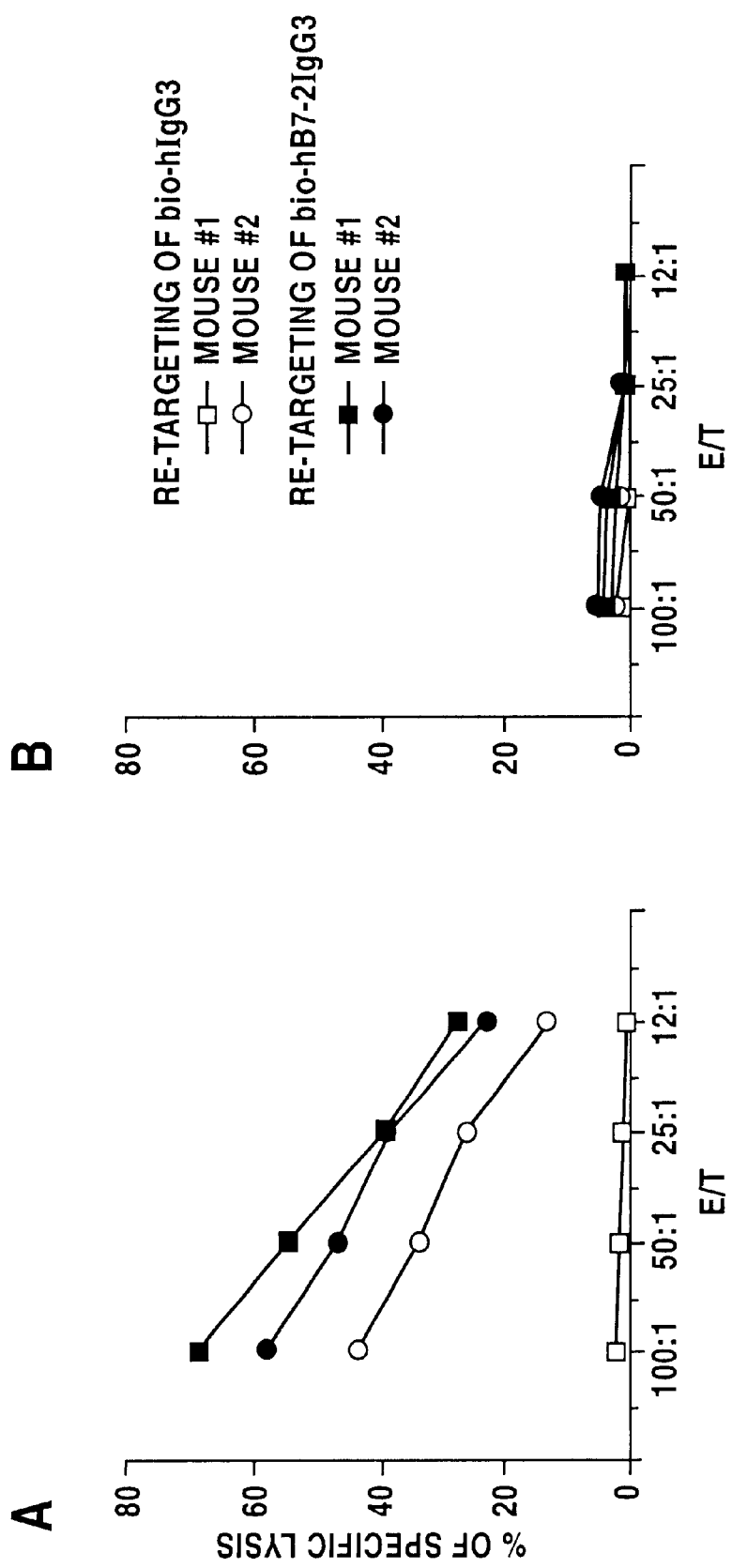
FIG. 10 shows the results of ex vivo cytotoxicity assays after restimulation of the spleen cells of RMA-T bearing mice 15 days from tumor inoculation, corresponding to 14 days after performing the three-step targeting of either bio-B7-2-IgG3 or human-IgG3.
Figure 11:
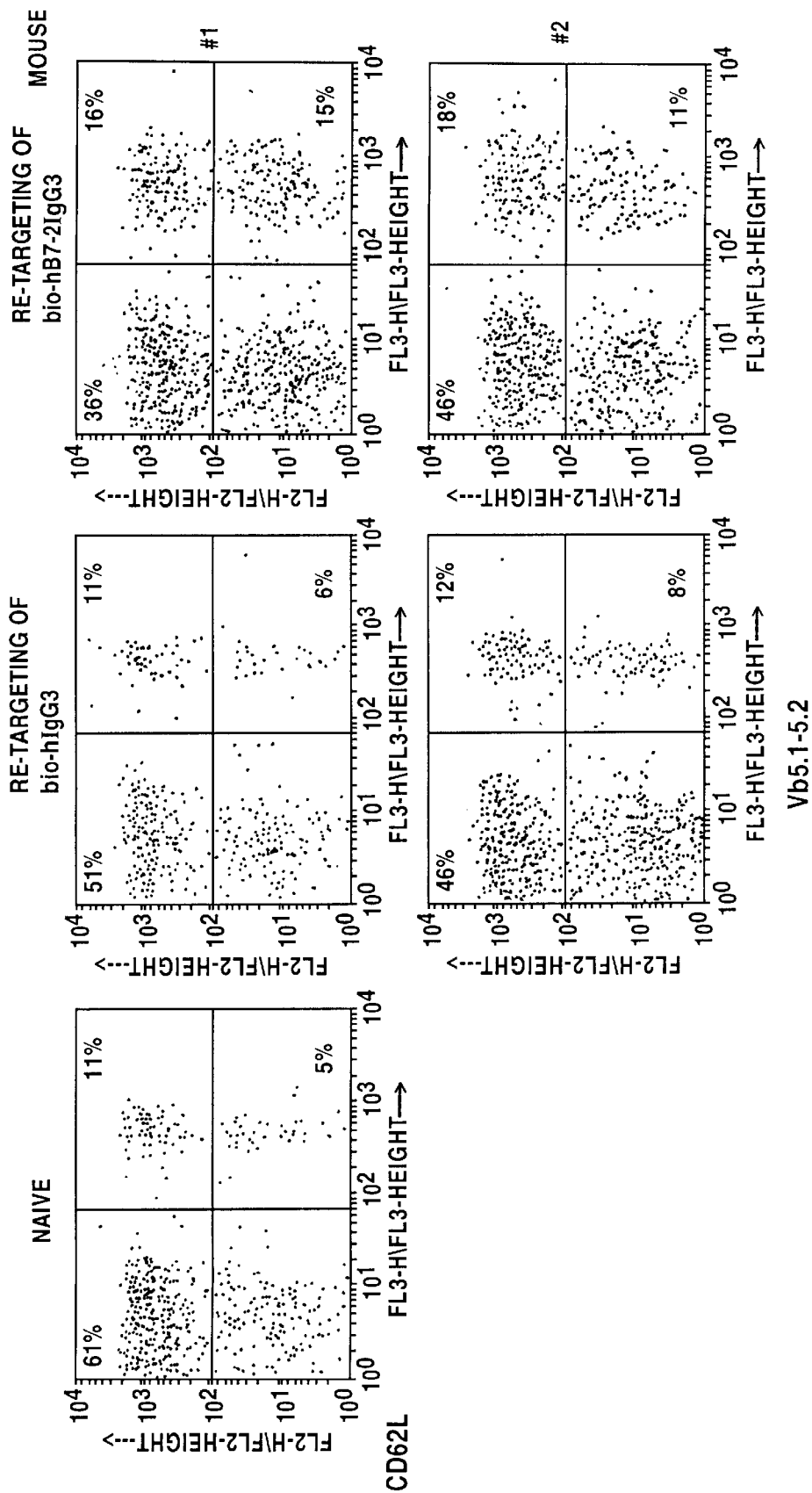
FIG. 11 shows in vivo targeting of bio-B7-2-Ig, but not of bio-h-IgG3, caused the expansion of activation-experienced $CD8^+TCRV\beta5^+CD62L^{low}$ splenic cells obtained from the same mice used in the killing experiment.

To analyze more in details this anti-RMA T cell response, ex vivo cytotoxicity assays were first performed by restimulating the spleen cells of RMA-T bearing mice 15 days from tumor inoculation, corresponding to 14 days after performing the three-step targeting of either bioB7-2-IgG3 or human-IgG3. Only the mice that received bio-B7-IgG3 as the third step developed a consistent RMA-specific CTL response, which was more potent then the one developed in one control mouse (FIG. 10A). Since the Rouscher virus-derived immuno-dominant epitope presented by RMA cells on $D^b$ is mainly recognized by CD8$^+$ CTLs expressing the TCRVβ5.1–5.2 region, a determination was made as to whether in vivo targeting of established RMA-T tumors by bio-B7-2-Ig resulted in a sizeable expansion of primed CD8$^+$Vβ5$^+$ T cells. As shown in FIG. 11, in vivo targeting of bio-B7 -2-Ig, but not of bio-h-IgG3, caused the expansion of activation-experienced CD8$^+$TCRVβ5$^+$ D62L$^{low}$ splenic T cells obtained from the same mice used in the killing experiment described above, although expanded CD8$^+$ TCRVβ5$^+$ T cells also expressed a CD62$^{high}$ phenotype. The expansion was specific for CD8$^+$ T cells expressing the TCR Vβ 5, since no significant expansion could be detected within CD8$^+$ CD62$^{low}$ T cells expressing control TCR Vβ 6, 8 and 13 (data not shown). These data therefore indicate that three-step tumor targeting in vivo with soluble B7-2-Ig costimulatory molecules markedly enhances the endogenous anti-tumor immunity, by determining the selective expansion of tumor-specific CTLs.

Therefore, the above experiments show that targeting tumors with bio-B7-2-Ig molecules is an efficient way to induce therapeutic anti-tumor immunity both in vitro and in vivo. In all respects, tumor cells expressing B7-2 molecules by somatic targeting of soluble recombinant B7-2-Ig molecules are as immunogenic as those expressing B7-2 after genetic transformation. Providing neoplastic cells a costimulatory signal by targeting soluble B7-2-Ig molecules, however, appears to be less time consuming than genetic transformation, and in principle does not require the generation of a long term cell line from each tumor. This would allow utilization of primary tumor material from surgical specimens, which could be armed by three-step method with B7-2-Ig molecules, irradiated, and injected back in the patient of origin within short time. Furthermore, the same approach could be exploited to induce and expand tumor-specific T cells in vitro, suitable for adoptive immunotherapy.

Besides its straightforward utilization in vitro, the above experiments demonstrated the efficacy of targeting soluble B7-2-Ig costimulatory molecules in vivo. This represents an unique feature of this approach, which is simplified by the use of the three-step mediated targeting system. There are several advantages in utilizing this targeting strategy: first, it is a modular approach that allows fine dosing of the amounts of each components utilized in the targeting. For instance, it would be possible to use high amounts of anti-tumor mAb and avidin, to ensure efficient avidination of all the tumor lesions, followed by limiting amounts of the last effector molecule. This is particularly important if one contemplates using in vivo cytokines, such as TNF-α or IFN-γ, chemotherapy agents, radioactive compounds or toxins which are extremely toxic at high systemic doses, but which can be exploited at low doses, when their activities are concentrated at the tumor site. Second, the three-step approach allows the simple combination of different biotinilated anti-tumor mAbs, as well as effector molecules, thus avoiding the requirement of generating corresponding bi-specific molecules, each carrying the desired tumor specificity and effector arm.

LIST OF REFERENCES

Anichini, A., et al., J. Exp. Med. 177 (1993) 989
Azuma, M., et al., J. Exp. Med. 175 (1992) 353–360
Azuma, M., et al., J. Exp. Med. 177 (1993) 845
Azuma, M., et al., J. Immunol. 149 (1992) 1115
Azuma, M., et al., J. Immunol. 115 (1993) 2091
Azuma, M., et al., Nature 366 (1993) 76
Boussiotis, V. A., et al., Proc. Natl. Acad. Sci. USA 19 (1993) 11059
Caux, C., et al., J. Exp. med. 180 (1995) 1841–1847
Cavallo, F., et al., Eur. J. Immunol. 25 (1995) 1154–1162
Chen, L., et al., Immunol. Today 14 (1993) 483
Chen, L., et al., J. Exp. Med. 179 (1994) 523
Dellabona, P., et al., J. Exp. Med. 177 (1993) 1763–1771
Freeman, G. J. et al., J. Immunol. 143 (1989) 2714–2722
Freeman, G. J., Science 262 (1993) 909–911
Greenberg, P. D., Adv. Immunol. 4 (1991) 281–355
Guinan, E. C., et al., Blood 84 (1994) 3261–3282
Harlow, E., and Lane, D., Antibodies, Cold Spring Harbor Laboratory (1988) 341
Hellström, K. E., et al., The Biologic Therapy of Cancer, J.B. Lippincot Co., Philadelphia (1991) p. 35
J. Cell Biochemistry Supplement 17E, page 203, abstract S210
Julius, M. H. et al., Eur. J. Immunol. 3 (1973) 645
Lanzavecchia, A., Nature 319 (1986) 765–767
Lindsten, T., et al., J. Immunol. 151 (1993) 3489
Lurquin et al., Cell 58 (1989) 293
McHugh, R. S., et al., Proc. Natl. Acad. Sci, USA 92 (1995) 8059–8063
Mueller, D. L., et al., Annu. Rev. Immunol. 7 (1989) 445
PCT/EP94/01573
Ramarathinam, L., et al., J. Exp. Med. 179 (1994) 1205
Riddel, R. R., et al., Science 257 (1992) 238–241
Townsend, A., and Bodmer, H., Ann. Rev. Immunol. 7 (1989) 601
Traunecker, A., et al., Nature 331 (1988) 84–86
Traunecker, A., et al., Immunology Today 10 (1989) 29–31
Vandenberghe, P., et al., Int. Immunol. 3 (1993) 229
Wiggler et al., Cell 1 (1977) 223
WO 92/05262
WO/92/08796
WO/95/03408
WO/95/06723

What is claimed is:

1. A method for producing MHC-restricted, activated tumor-specific T cells, comprising the following steps:
   (1) obtaining tumor cells from a patient;
   (2) inhibiting the proliferation of the tumor cells and incubating said tumor cells with reagents comprising a ternary complex consisting essentially of
      (i) a biotinylated antibody against a cell surface antigen of said tumor cells from said patient or at least two Fab fragments of said antibody,
      (ii) a ligand which is avidin, streptavidin or neutravidin, and
      (iii) biotinylated B7-Ig,
   to generate targeted tumor cells;
   (3) obtaining T cells from said patient; thereafter
   (4) co-cultivating said targeted tumor cells with said T cells to activate said T cells in the presence of at least interleukin 2; and thereafter
   (5) isolating said activated T cells from the targeted tumor cells to obtain activated tumor-specific T cells.

2. The method of claim 1, further comprising marking said T cells prior to or after step (4).

3. The method of claim 1, wherein said T cells are obtained from peripheral blood mononuclear cells with the exclusion of B cells and monocytes.

4. The method of claim 1, wherein said T cells are $CD4^+$ and/or $CD8^+$ lymphocytes.

5. The method of claim 1, wherein said T cells are purified $CD8^+$ lymphocytes and tumor-infiltrating T cells.

6. The method of claim 2, wherein said T cells are marked by transfecting said T cells with a gene which codes for a marker protein expressed on the surface of said T cells.

7. The method of claim 6, wherein said marker protein is CD24.

8. The method of claim 1, further comprising transfecting said T cells with a suicide gene, which gene directly or indirectly kills said T cells in order to reduce the number of activated tumor-specific T cells when needed.

9. The method of claim 8, wherein said suicide gene is a thymidine kinase gene.

10. The method of claim 1, wherein the proliferation of the tumor cells is inhibited by exposing said tumor cells to an effective amount of ionizing irradiation and/or mitomycin C.

11. The method of claim 1, wherein the inhibition of the proliferation of said tumor cells is conducted before the incubating step.

12. The method of claim 1, wherein said T cells and said tumor cells are co-cultivated at a ratio of about 100:1 to about 5:1.

13. The method of claim 1, wherein said tumor cells are taken from a surgical specimen of said patient.

14. The method of claim 1, wherein the inhibition of the proliferation of said tumor cells is conducted after the incubating step.

15. The method of claim 1, wherein said B7 protein is B7-1 or B7-2.

16. The method of claim 1, wherein said cell surface antigen is ERB B2 or a transferrin receptor.

17. The method of claim 1, wherein step (4) is carried out by co-cultivating said targeted tumor cells with said T cells in the presence of at least one other lymphokine to stimulate said T cells.

18. The method of claim 17, wherein said lymphokine is IL-6, IL-7 or a combination thereof.

19. The method of claim 17, further comprising, between steps (4) and (5), restimulating said T cells at least once by isolating said T cells and co-cultivating said isolated T cells with said pre-targeted tumor cells and said at least one other lymphokine in order to increase the number of activated tumor-specific T cells.

20. A method of treating a tumor in a patient, comprising the steps of:
   (A) obtaining tumor cells from said patient,
   (B) inhibiting proliferation of said tumor cells and incubating said tumor cells with reagents comprising a ternary complex consisting essentially of
      i) a biotinylated antibody against a cell surface antigen of said tumor cells from said patient or at least two Fab fragments of said antibody,
      ii) a ligand which is avidin, streptavidin or neutravidin, and
      iii) biotinylated B7-Ig,
   (C) obtaining T cells from said patient, and thereafter
   (D) co-cultivating said tumor cells of step (B) with said T cells to activate said T cells in the presence of at least interleukin 2, and thereafter
   (E) isolating T cells from said tumor cells to obtain MHC-restricted, activated tumor-specific T cells, and thereafter
   (F) administering an effective amount of said MHC-restricted, activated tumor-specific T cells to said patient.

21. The method of claim 20, wherein about $10^7$ to about $10^9$ activated tumor-specific T cells per square meter of body surface area are infused intravenously.

22. The method of claim 21, wherein the intravenous infusion is repeated once every four weeks.

23. The method of claim 20, further comprising marking said T cells prior to or after step (4) in order to monitor the persistence of said activated tumor-specific T cells in said patient.

24. The method of claim 20, further comprising transfecting said T cells with a suicide gene, which gene directly or indirectly kills said T cells to reduce the number of activated tumor-specific T cells in order to terminate the treatment when needed.

25. A method for producing MHC-restricted, activated tumor-specific T cells, comprising the following steps:
   (1) obtaining tumor cells from a patient;
   (2) inhibiting the proliferation of the tumor cells and conducting a three-step procedure:
      I. incubating said tumor cells with a biotinylated antibody against a cell surface antigen of said tumor cells from said patient or at least two Fab fragments of said antibody to obtain a product of step I;
      II. incubating the product of step I with a ligand which is avidin, streptavidin or neutravidin to obtain a product of step II; and
      III. incubating the product of step II with biotinylated B7-Ig to generate targeted tumor cells;
   (3) obtaining T cells from said patient;
   (4) co-cultivating said targeted tumor cells with said T cells to activate said T cells in the presence of at least interleukin 2; and thereafter
   (5) isolating said T cells from the targeted tumor cells to obtain activated tumor-specific T cells.

26. The method of claim 25, further comprising marking said T cells prior to or after step (4).

27. The method of claim 25, wherein said T cells are obtained from peripheral blood mononuclear cells with the exclusion of B cells and monocytes.

28. The method of claim 25, wherein said T cells are CD4+ and/or CD8+ lymphocytes.

29. The method of claim 25, wherein said T cells are purified CD8+ lymphocytes and tumor-infiltrating T cells.

30. The method of claim 26, wherein said T cells are marked by transfecting said T cells with a gene which codes for a marker protein expressed on the surface of said T cells.

31. The method of claim 30, wherein said marker protein is CD24.

32. The method of claim 25, further comprising transfecting said T cells with a suicide gene, which gene directly or indirectly kills said T cells in order to reduce the number of activated tumor-specific T cells when needed.

33. The method of claim 32, wherein said suicide gene is a thymidine kinase gene.

34. The method of claim 25, wherein the proliferation of the tumor cells is inhibited by exposing said tumor cells to an effective amount of ionizing irradiation and/or mitomycin C.

35. The method of claim 25, wherein the inhibition of the proliferation of said tumor cells is conducted before step I.

36. The method of claim 25, wherein said T cells and said tumor cells are co-cultivated at a ratio of about 10:1 to about 5:1.

37. The method of claim 25, wherein said tumor cells are taken from a surgical specimen of said patient.

38. The method of claim 25, wherein the inhibition of the proliferation of said tumor cells is conducted after step III.

39. The method of claim 25, wherein said B7 protein is B7-1 or B7-2.

40. The method of claim 25, wherein said cell surface antigen is ERB B2 or a transferrin receptor.

41. The method of claim 25, wherein step (4) is carried out by co-cultivating said targeted tumor cells with said T cells in the presence of at least one other lymphokine to stimulate said T cells.

42. The method of claim 41, wherein said lymphokine is IL-6, IL-7 or a combination thereof.

43. The method of claim 41, further comprising, between steps (4) and (5), restimulating said T cells at least once by isolating said T cells and co-cultivating said isolated T cells with said pre-targeted tumor cells and said at least one other lymphokine in order to increase the number of activated tumor-specific T cells.

44. A method of treating tumors in a patient, comprising the following steps:

(A) obtaining tumor cells from said patient;

(B) inhibiting the proliferation of said tumor cells and conducting a three-step procedure:
  I. incubating said tumor cells with a biotinylated antibody against a cell surface antigen of said tumor cells from said patient or at least two Fab fragments of said antibody to obtain a product of step I;
  II. incubating the product of step I with a ligand which is avidin, streptavidin or neutravidin to obtain a product of step II; and
  III. incubating the product of step II with biotinylated B7-Ig to generate targeted tumor cells;

(C) obtaining T cells from said patient;

(D) co-cultivating said targeted tumor cells with said T cells to activate said T cells in the presence of at least interleukin 2; and thereafter (E) isolating said T cells from said targeted tumor cells to obtain MHC-restricted, activated tumor-specific T cells, and thereafter (F) administering an effective amount of said MHC-restricted, activated tumor-specific T cells to said patient.

45. The method of claim 44, wherein the activated tumor-specific T cells are administered intravenously to said patient.

46. The method of claim 45, wherein about $10^7$ to about $10^9$ activated tumor-specific T cells per square meter of body surface area are infused intravenously.

47. The method of claim 45, wherein the intravenous infusion is repeated once every four weeks.

48. The method of claim 44, further comprising marking said T cells prior to or after step (4) in order to monitor the persistence of said activated tumor-specific T cells in said patient.

49. The method of claim 44, further comprising transfecting said T cells with a suicide gene, which gene directly or indirectly kills said T cells to reduce the number of activated tumor-specific T cells in order to terminate the treatment when needed.

50. The method of claim 1, further comprising forming said ternary complex at the end of step 2).

* * * * *